United States Patent
Cho et al.

(10) Patent No.: US 7,704,957 B2
(45) Date of Patent: Apr. 27, 2010

(54) **COMPOSITION FOR INHIBITING HIV ACTIVITY EXTRACTED FROM *PAECILOMYCES* SP. (TOCHU-KASO) J300**

(75) Inventors: Sae-Yun Cho, Geonggi-do (KR); Sang-Duk Ji, Geonggi-do (KR); Seong-Kyu Song, Geongbuk (KR); Kwan-Hee Lee, Geongbuk (KR)

(73) Assignee: Rural Development Administration, Kyunggi-do (KR)

( * ) Notice: Subject to any disclaimer, the term of this patent is extended or adjusted under 35 U.S.C. 154(b) by 1047 days.

(21) Appl. No.: 10/474,292

(22) PCT Filed: Apr. 9, 2002

(86) PCT No.: PCT/KR02/00625

§ 371 (c)(1),
(2), (4) Date: Jan. 6, 2004

(87) PCT Pub. No.: WO02/080921

PCT Pub. Date: Oct. 17, 2002

(65) Prior Publication Data

US 2004/0121963 A1    Jun. 24, 2004

(30) Foreign Application Priority Data

Apr. 9, 2001  (KR) ................... 2001-18664
Apr. 9, 2001  (KR) ................... 2001-18665

(51) Int. Cl.
  *A61K 38/00*    (2006.01)
  *A61K 31/4965*  (2006.01)
  *A61K 35/00*    (2006.01)
(52) U.S. Cl. .............. 514/19; 514/255.02; 424/780
(58) Field of Classification Search ........... 514/19, 514/255.02; 424/780
  See application file for complete search history.

(56) References Cited

U.S. PATENT DOCUMENTS 4,416,871 A * 11/1983 Walter et al. ............. 514/18

(Continued)

FOREIGN PATENT DOCUMENTS

EP        498680 A1       8/1991

(Continued)

OTHER PUBLICATIONS

Stewart et al; "Surface-Enhanced Raman Spectroscopy of Peptides and Proteins Absorbed on an Electrochemically Prepared Silver Surface"; In: Spectrochimica Acta Part A, Jul. 1999, vol. 55, pp. 1615-1640.

(Continued)

*Primary Examiner*—Shengjun Wang
(74) *Attorney, Agent, or Firm*—Nixon & Vanderhye P.C.

(57) ABSTRACT

The present invention relates to a composition for inhibiting HIV activity comprising the extract of *Paecilomyces* sp. (Tochu-kaso) J300. More particularly, the present invention relates to a composition for inhibiting HIV activity comprising 3-[5-(methoxy-ethyl)-3,6-dioxo-piperazine-2-yl]propionic acid represented by Formula 1 and 4-methyl-2-[(pyrrolidine-2-carbonyl)-2-amino]pentanoic acid represented by Formula 2 that are extracted from *Paecilomyces* sp. (Tochu-kaso) J300; and to a medical composition and food composition containing the same.

[Formula 1]

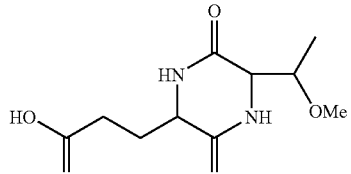

[Formula 2]

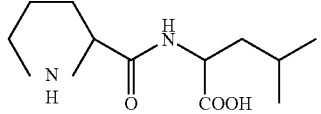

3 Claims, 24 Drawing Sheets

U.S. PATENT DOCUMENTS

| | | | | |
|---|---|---|---|---|
| 5,558,866 A | * | 9/1996 | D'Arrigo | 424/777 |
| 5,939,310 A | * | 8/1999 | Cho et al. | 435/254.1 |
| 5,948,404 A | * | 9/1999 | Taketomo et al. | 424/115 |

FOREIGN PATENT DOCUMENTS

| | | | |
|---|---|---|---|
| EP | 472077 A2 | | 2/1992 |
| JP | 1997-025237 | | 1/1997 |
| JP | 10-164978 | | 6/1998 |
| WO | WO 99/21961 | * | 5/1999 |

OTHER PUBLICATIONS

Stewart et al, "Surface-enhanced Raman spectroscopy of peptides and proteins adsorbed on an electrochemically prepared silver surface", Spectrochemica Acta Part A, vol. 55, 1999, pp. 1615-1640 (D1).

Nakamura et al, "Activation of In Vivo Kupffer Cell Function . . . ", Japan J. Pharmacol., 79, 505-508 (1999).

Stewart, S. et al, 1999. vol. 55, No. 7-8, pp. 1615-1640.

Hellberg, Sven et al, 1991, vol. 37, No. 5, pp. 414-424.

Dickinson, S.L. et al, Peptides, 1981, vol. 2, No. 2, pp. 189-195.

Shin et al, "Antioxidant and Immunostimulating Activities of the Fruiting Bodies . . . ", Reprinted from Healthy Aging for Functional Longevity, vol. 928 of the Annals of the New York Academy of Sciences, Apr. 2001.

* cited by examiner

COMPOSITION FOR INHIBITING HIV ACTIVITY EXTRACTED FROM *PAECILOMYCES* SP. (TOCHU-KASO) J300

This application is the US national phase of international application PCT/KR02/00625 filed 9 Apr. 2002, which designated the US. PCT/KR02/00625 claims priority of KR Application No. 2001/18665 filed 9 Apr. 2001 and KR Application No. 2001/18664 filed 9 Apr. 2001. The entire contents of these applications are incorporated herein by reference.

BACKGROUND OF THE INVENTION

1. Field of the Invention

The present invention relates to a composition for inhibiting HIV activity comprising the extract of *Paecilomyces* sp. (Tochu-kaso) J300. More particularly, the present invention relates to a pharmaceutical composition for inhibiting HIV activity comprising 3-[5-(methoxy-ethyl)-3,6-dioxo-piperazine-2-yl]propionic acid represented by Formula 1, 4-methyl-2-[(pyrolidine-2-carbonyl)-2-amino]pentanoic acid represented by Formula 2 or derivatives thereof that can be extracted from *Paecilomyces* sp. (Tochu-kaso) J300; and to a and food composition containing the same.

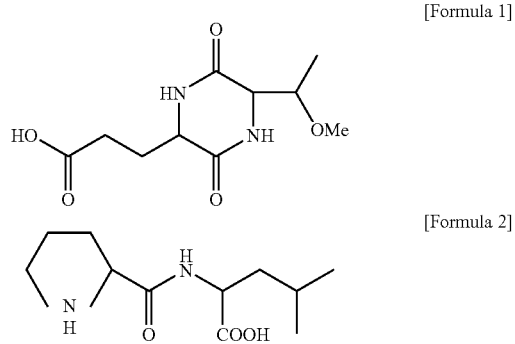

[Formula 1]

[Formula 2]

2. Description of the Related Arts

From the ancient time, the tochu-kaso was regarded as miraculous medicine, and especially, Chinese Emperor Jinsihwang took the tochu-kaso as perpetual youth and longevity. Further, the recent reports disclose that tochu-kaso has the effect of anti-exhaustion, immunity-increasing and anti-tumor activities, etc. (Natural Products Research Institute of Seoul National University). The various effects of the tochu-kaso are thought to originate from the various components of the tochu-kaso and its direct or indirect relation to the homeostasis of the human body.

There are 300 kinds of tochu-kasos are known in the world, but the size and the number of the population is small, and that, it is difficult to obtain them commercially and even samples for research are not sufficient. Therefore, Rural Development Administration of Korea has invented a the method for cultivating the tochu-kaso by inoculating the spores of the tochu-kaso into a larva of silkworm. In the year of 2000, the method of cultivation is discovered for 5 kinds of tochu-kasos including *Paecilomyces japonica*. *Paecilomyces* sp. J300 (Tochu-kaso J300) is obtained by inoculating the spores of the *Paecilomyces* sp. J300 into a larva of silkworm, and the method for cultivating the tochu-kaso J300 is disclosed Korean Patent No 187,897 and U.S. Pat. No. 5,939,310.

According to UNAIDS and WHO, there are more than thirty million (30,000,000) people who are infected by HIV in the year of 1997 throughout the world. The number of people newly infected by HIV in the year 1997 is about 5,800,000 and 590,000 of those are children. With this increase, the number of people infected by HIV seems to be forty million (40,000,000) in the year of 2000. More than 90% of the infected are living in the developing countries, and most of the infected do not know the fact that they are infected, which is a serious problem.

Therefore, eliminating AIDS is an international issue, and a new medicine or medical composition to eliminate AIDS without side effects are eagerly being sought.

After the first sufferer of AIDS is reported in 1981, HIV, the AIDS Virus was separated and identified from a sufferer of AIDS in 1984, and HIV is convinced to be main cause of the AIDS. Therefore, to treat AIDS, searching for anti-HIV material is widely performed. As the result, AZT, the most famous AIDS treatment, was invented in 1987, and at the time of February 1999, there are 13 kinds of drugs approved by FDA and sold as AIDS treatment. However, the conventional treatment for AIDS has the problems that resistant virus is generated and side effect is observed, and therefore, there are limitations in the treatments.

To overcome or reduce the limitations, many pharmaceutical companies and research centers are searching for new and developed AIDS treatments.

HIV (Human Immunodeficiency Virus) was disclosed to be cause of AIDS by being separated and identified from a sufferer of AIDS in 1984. At the beginning of the disclosure, HIV infection was misunderstood to be restricted only to homosexual or some under developed countries, but now, it is regarded as the worldwide prevalent infectious disease and a serious social problem.

HIV is classified in the retrovirus, more specifically, in the lentivirus group. The size of the HIV is about 10 micron and the outer surface is covered with phospholipid like other cells, and two virus genomes of RNA are protected by capsid (core protein) therein. These HIV genomes consist of ten (10) units of genes, which is a lot of genes compared with the size of total genome.

HIV infection is accomplished by the conjugation of the envelop protein (gp120) that exists on the surface of the virus and receptor that exists on the surface of the target cell. The above receptor is a kind of surface protein molecule of cell called CD4 antibody, and CD4 T cell (helper T cell) or macrophage is main target of the HIV because they have a lot of CD4 antibodies on the surface thereof. By the conjugation of the virus and the cell, the phospholipid envelop of the virus is infused into the cell surface, and virus genome and nucleus protein are flowed into the cell. At this moment, the virus genome is reverse transcribed into DNA from RNA by the reverse transcriptase of the virus, then transported into the nucleus of the cell and inserted into the genome of the host cell. This procedure is one of the characteristic features of the retrovirus. The HIV conceals itself in the most safe region of the host cell, and is supplied with all the materials and nutritions needed for growth. Further, the HIV suppresses or accelerates its growth according to the surroundings and conditions thereof to protect itself from the outer antibody etc.

AIDS viruses are divided tow main groups, that are, HIV-1 and HIV-2. The HIV-1 is generally called as 'AIDS virus' because it is generally found various sufferers throughout the world including Korea. HIV-2 that is found from the sufferer s of the West Africa has only 55% of homologies with the HIV-1 in the base sequence, and is more similar to SIV (Simian Immunodeficiency Virus) that is monkey's AIDS virus. The toxicity of the HIV-2 is known to be weaker than HIV-1.

HIV has much variety in the viewpoints of biology as well as genetics. Base sequences of the HIV obtained from the sufferers are different each other. And, even when the base sequence is obtained from one sufferer, it is different according the state of progress. Further, when the viruses are obtained with a uniform time intervals, the base sequence is different according to the tissues. These various base sequence relates to the biological characteristics of the virus very much. The different viruses having different base sequence have different affinity of infection to a certain cell, rate of proliferation, generation of virus, toxicity to a cell, generation rate of multinucleate giant cell, latent period and activity period, sensitivity to the neutralizing antibody, etc.

According to examination result for the relation betweens these various biological characteristics and the onset of the AIDS, the viruses that obtained from the initially infected sufferer do not form a multinucleate giant cell (NSI: Nonsyncytia-Inducing), but are mainly infected via macrophage. However, as the AIDS proceeds to the terminal state, the SI (Syncytia-Inducing) increase, and the virus changes to be a virus that is likely to infected by helper T cell instead of macrophage. This suggests that the biological characteristics of the HIV and onset of the disease have relations each other.

When one week is passed after HIV infection, proliferation of virus increases, and that, the virus is easily found in the blood of the sufferer. This stage is called as viremia. After 1 or 2 week later, the number of virus dramatically decreases under the level not to be separated. This latent period is maintained for a long time, then the proliferation of virus becomes active to develop for AIDS and becomes the state of viremia again. However, a recent research based on the study of chain polymerization with polymerase reported that virus is continuously generated in the latent period.

The number of CD4 cell dramatically decreases in the first viremia, and when the proliferation of the virus decreases the number of CD4 cell is recovered to its normal state. (The number of CD4 cell of the healthy adult is 500-1000 CD4 cells/mm$^3$). When the number of CD4 cells decrease under 200 cells/mm$^3$, it develops as ARC (AIDS-related Complex) or AIDS. Because the rate of opportunistic infection increases for the AIDS sufferers, they mainly die from Pneumocysitis carinii.

The periods that the number of HIV dramatically decreases and that the number of CD8 cells increases coincide, and CD8 T cell is known as to inhibit the growth of cells or to kill the cells infected by virus. Therefore, CD8 cell shows an important immunity effect for the initially infected viruses. Antibody is generated after the virus decreases. CD 8 cell and antibody are detected from the beginning of the infection to the onset of AIDS, but their activities become disappeared and in some cases they promote the virus infection. The reason why the immunity system that showed anti-virus activity at the beginning of the infection loses its activity is a subject to be solved. Because AIDS outbreaks only in the human body, the research is limited and the understanding of this disease is very rudimentary.

The researchers agree that the cause of the Immune Deficiency is the decrease of the CD4 cell, however, they have different opinions regarding the mechanism that HIV decreases the CD4 cell. For the explanation of the CD4 cell decrease, there are many theories such as generation of multinucleate giant cell, stimulation of virus DNA that is not inserted, the influence by the constitution of the host cell membrane, programmed abandonment of death of the cell, secretion of toxic material from the infected cell, cell destruction by auto-immunity, et al. However, nothing was proved in vivo. Further, many researches have been made to figure out the symptom of HIV disease by using monkey and monkey's AIDS virus, SIV, but no significant discovery was not accomplished.

In the meantime, AZT (Zidovudine), regarded as the representative of AIDS treatment, is a drug that inhibits the activity of the HIV reverse transcriptase and its effects are widely studied. AZT improves the condition of the sufferer when used at the initial state of infection, however it cannot lengthen the lifetime of the sufferer. Further, it has a toxic influence to the marrow and resistant virus is generated when used for a long time. Therefore, it has a limitation for the AIDS treatment. As for DDI, DDC, d4T etc. that are approved by FDA for the treatment of AIDS, resistant viruses have been generated, but they are not so toxic as AZT. Recently, a theory suggesting that using the above drugs together can reduce or inhibit the toxicity and generation of resistant virus as well as can increase the therapeutic effects is reported. To clarify the suggestion, a lot of research institutes have performed clinical tests, and positive results were obtained.

In addition to the above research, there are a lot of smart and novel methods for inhibiting the growth of AIDS virus are invented and testified. For example, a method preventing the virus from accessing to cells, a method selectively destructing virus-infected cells, a therapeutic method of using a drug for inhibiting the important activity of enzyme for the growth of virus (such as protease, integrase, tat inhibitor, rev inhibitor) or cytokine, a method of inserting CD8 cell, gene therapeutics etc. are suggested.

There was significant improvement in the research of the HIV vaccine. Various methods such as using died virus or attenuated virus, using subunit vaccine by genetic engineering, using anti-idio type antibody, injecting DNA gene etc. were developed. The problem of developing vaccine is that the virus is too various. For example, after vaccination, when using the original virus used for above vaccine the disease is contracted, the growth of virus is suppressed by the antibody; however, when the disease is contracted by using newly infected cell or virus, no suppression was observed. It is a subject for the inventors to overcome the variety of the viruses. In addition to the vaccine using body fluid, the vaccines using cell immune method with CD8 cell or mucosal immunity should be developed, and more effective results are expected by mixing the vaccines.

Under these circumstances, the present inventors studied to develop a new AIDS treatment without side effects and generation of the resistant virus.

As the result, the inventors found that the extract of J300 Tochu-kaso contains anti HIV activity, and analyzed the active fraction to find out active component, further, the active component was synthesized by chemically to provide novel AIDS treatment with low toxicity and side effect.

SUMMARY OF THE INVENTION

The present invention provides a composition for inhibiting HIV activity comprising the extract of Tochu-kaso J300.

Further, the present invention provides 3-[5-(methoxyethyl)-3,6-dioxo-piperazine-2-yl]propionic acid represented by Formula 1 and 4-methyl-2-[(pyrolidine-2-carbonyl)-2- amino]pentanoic acid represented by Formula 2 and derivatives thereof that can be extracted from Tochu-kaso J300 and showing anti HIV activity.

[Formula 1]

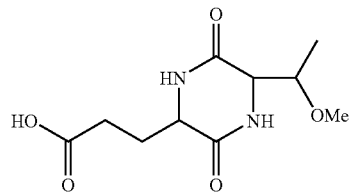

[Formula 2]

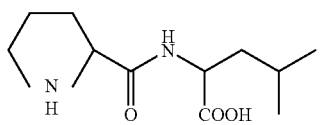

Further, the present invention provides a composition for inhibiting HIV activity, a drug composition for treating AIDS and food composition for treating AIDS that comprise 3-[5-(methoxy-ethyl)-3,6-dioxo-piperazine-2-yl]propionic acid and 4-methyl-2-[(pyrolidine-2-carbonyl)-2-amino]pentanoic acid and/or derivatives thereof.

DETAILED DESCRIPTION OF THE INVENTION

In the present invention, to certify the anti-HIV activity of the Tochu-kaso, the extracts of three kinds of Tochu-kasos including *Paecilomyces japonica*, *Paecilomyces farinosa* and *Paecilomyces* sp. J300 (Tochu-kaso J300) were studied by obtaining the extracts from the frozen dried powders thereof. As the result, it is found that the aqueous extract of Tochu-kaso J300 has the anti-HIV activity.

Rural Development Administration of Korea first cultivated the Tochu-kaso J300, by inoculating the spores of the tochu-kaso into a larva of silkworm classified in Paecilomyces sp. For reference, *Paecilomyces* sp. J300 used for cultivating Tochu-kaso J300 has been deposited with Korean Culture Collection of Microorganisms attached to the Korean Foundation of Culture Collections (KFCC) on Nov. 29, 1996 to receive an accession number "KFCC-100938", and the deposit was converted into the deposit under Budapest Treaty on Nov. 27, 1997 with an accession number of "KCCM 10116". And the method for cultivating the tochu-kaso J300 is disclosed in Korean Patent No 187,897 and U.S. Pat. No. 5,930,310.

3-[5-(methoxy-ethyl)-3,6-dioxo-piperazine-2-yl]propionic acid represented by above Formula 1 and 4-methyl-2-[(pyrolidine-2-carbonyl)-2-amino]pentanoic acid represented by above Formula 2 are extracted from Tochu-kaso J300 for the first time, however, which can be prepared by organic synthetic method.

At first, 3-[5-(methoxy-ethyl)-3,6-dioxo-piperazine-2-yl] propionic acid represented by Formula 1 is prepared by the following steps.

1) Amination of L-Boc-Glu and L-Threonine (GT-2)

Preparation of 2-(2-tert-butoxycarbonylamino-4-methoxycarbonyl-butyrylamino)-3-hydroxy-butyric acid methyl ester

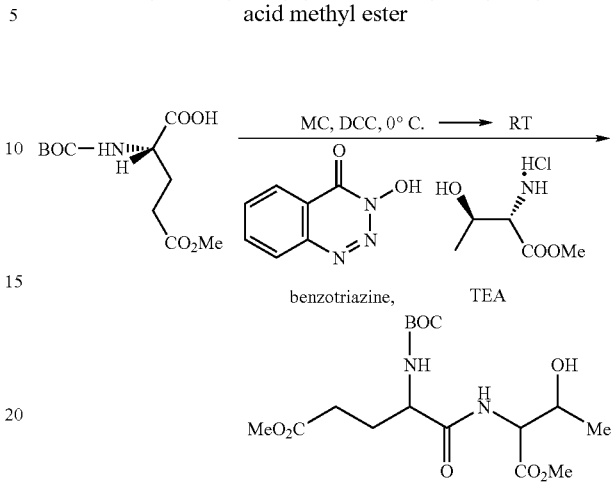

L-Boc-glutamic acid 5-methylester and 3-hydroxy-benzo-triazine-(H)-4-one are dissolved in anhydrous methylenechloride (MC). DCC is added under $N_2$ and cooled and stirred for 10 minutes. A solution of L-threonine methyl ester hydrochloride and TEA in anhydrous MC is added to the above solution and stirred for 3 hours. The mixture is filtered off urea and the filtrate is extracted with MC and water. The organic layer is extracted with sat. $NaHCO_3$ and brine. The organic extract is dried and then evaporated. The final product is purified, preferably, on silica gel column using hexane: ethylacetate=2:1.

The above obtained [2-(2-tert-butoxycarbonylamino-4-methoxycarbonyl-butyrylamino)-3-hydroxy-butyric acid methyl ester] is called as "GT-2".

2) Removal of BOC Group (GT-3)

Preparation of 2-(2-Amino-4-methoxycarbonyl-butyrylamino)-3-hydroxy-butyric acid methyl ester

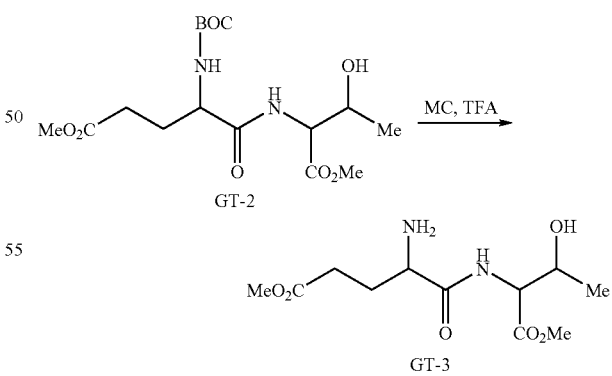

A solution of GT-2 in $CH_2Cl_2$ is treated with TFA and stirred at room temperature for 12 hours. Then, the solvent is evaporated and dried.

The above obtained 2-(2-Amino-4-methoxycarbonyl-butyrylamino)-3-hydroxy-butyric acid methyl ester is called as "GT-3".

3) Cyclization (GT-4)

Preparation of 3-[5-(1-Hydroxy-ethyl)-3,6-dioxo-piperazin-2-yl]-propionic acid methyl ester

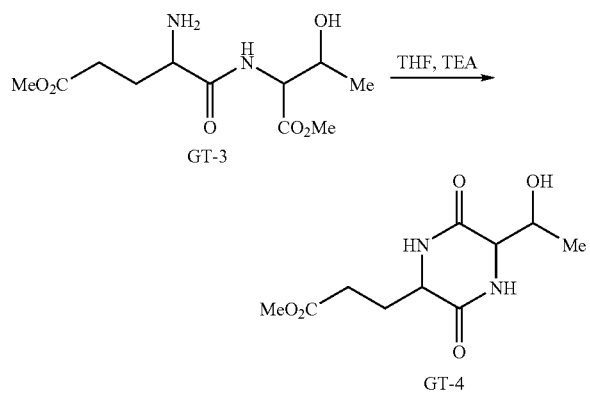

A solution of GT-3 in THF is treated with TEA and stirred at room temperature for 12 hours. The mixture is extracted with MC and water. The aqueous layer is extracted twice with MC. The organic extract is dried with $Mg_2SO_4$ and then evaporated. The final product is purified, preferably, on silica gel column using hexane:ethylacetate=4:1.

The above obtained 3-[5-(1-hydroxy-ethyl)-3,6-dioxo-piperazin-2-yl]-propionic acid methyl ester is called as "GT-4".

4) Decarboxylation (GT-5)

Preparation of 3-[5-(1-Hydroxy-ethyl)-3,6-dioxo-piperazin-2-yl]-propionic acid

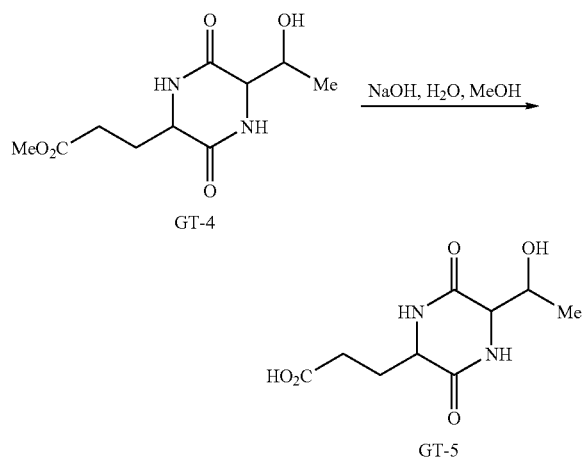

A solution of GT-4 in $H_2O$ is treated with 20% NaOH and stirred at room temperature for 30 min. Then, the solvent is evaporated for dryness. The final product is purified, preferably, on silica gel column using ethyl acetate:MeOH=2:1.

The above obtained 3-[5-(1-Hydroxy-ethyl)-3,6-dioxo-piperazin-2-yl]-propionic acid is called as "GT-5".

5) Deprotection and Methylation

The above obtained GT-5 undergoes deprotection and methylation to obtain 3-[5-(methoxy-ethyl)-3,6-dioxo-piperazine-2-yl]propionic acid.

On the other hand, 4-methyl-2-[(pyrolidine-2-carbonyl)-2-amino]pentanoic acid represented by Formula 2 is prepared by the following steps.

1) Amination of L-Boc-Proline and L-Leucine (LP-3)

Preparation of 2-(1-Methoxycarbonyl-3-methyl-butylcarbamoyl)-pyrrolidine-1-carboxylic acid tert-butyl ester

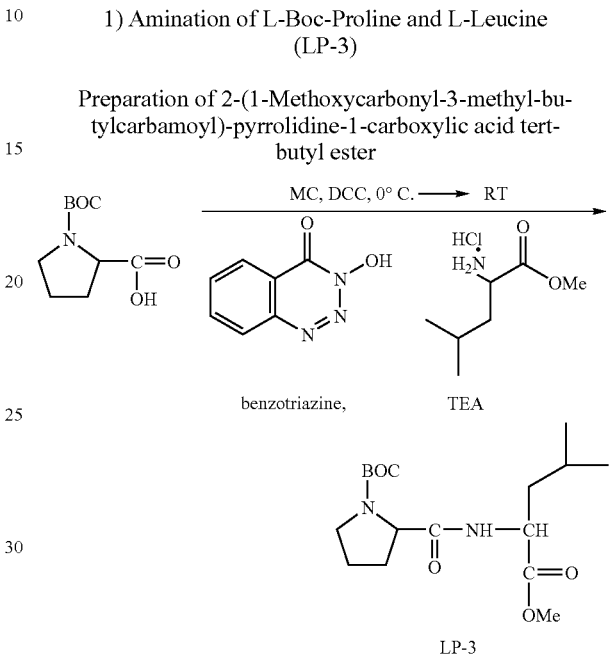

L-Boc-Proline and 3-hydroxy-benzotriazine-2(H)-4-one are dissolved in anhydrous MC (methylene chloride). DCC is added under. $N_2$ and cooled and stirred for 10 minutes. A solution of L-leucine methyl ester 5 and TEA in a little anhydrous DMF and anhydrous MC is added to the above solution and stirred for 15 hours. The mixture is filtered off urea and the filtrate is extracted with MC and water. The aqueous layer is extracted twice with MC. The organic extract is dried with $Mg_2SO_4$ and then evaporated. The final product is purified, preferably, on silica gel column using hexane:ethylacetate=4:1.

The above obtained 2-(1-Methoxycarbonyl-3-methyl-butylcarbamoyl)-pyrrolidine-1-carboxylic acid tert-butyl ester is called as "LP-3".

2) Removal of BOC Group (LP-4)

Preparation of 4-Methyl-2-[(pyrrolidine-2-carbonyl)-amino]-pentanoic acid methyl ester

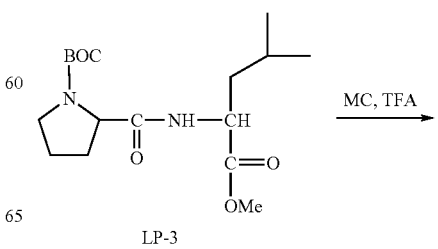

-continued

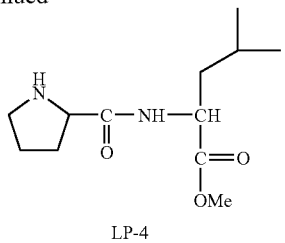

LP-4

A solution of LP-3 in $CH_2Cl_2$ is treated with TFA and stirred at room temperature for 12 hours. Then, the solvent is evaporated for dryness. The final product is purified, preferably, on silica gel column using ethylacetate:MeOH=20:1.

The above obtained 4-Methyl-2-[(pyrrolidine-2-carbonyl)-amino]-pentanoic acid methyl ester is called as "LP-4".

3) Hydrolysis (LP-5)

Preparation of 4-Methyl-2-[(pyrrolidine-2-carbonyl)-2-amino]pentanoic acid

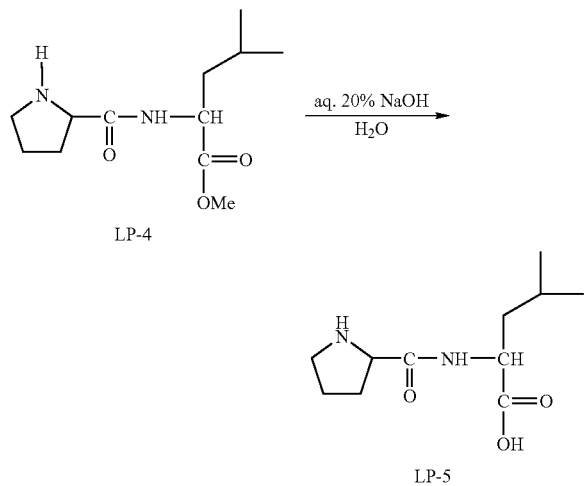

A solution of LP-4 in $H_2O$ is treated with 20% NaOH and stirred at room temperature for 30 min. Then, the solvent is evaporated for dryness. The final product is purified, preferably, on silica gel column using ethylacetate:MeOH=2:1.

Further, a person ordinary skilled in the art can prepare the derivatives of the 3-[5-(methoxy-ethyl)-3,6-dioxo-piperazine-2-yl]propionic acid and 4-methyl-2-[(pyrolidine-2-carbonyl)-2-amino]pentanoic acid without difficulty.

In addition, the composition for inhibiting HIV activity, a drug for treating AIDS and food composition for treating AIDS that comprise 3-[5-(methoxy-ethyl)-3,6-dioxo-piperazine-2-yl]propionic acid and 4-methyl-2-[(pyrolidine-2-carbonyl)-2-amino]pentanoic acid and/or derivatives also can be easily made by one skilled in the art without limitation in the formation.

The composition for inhibiting HIV activity or a drug composition for treating AIDS of the present invention comprise the compound of Formula 1 and/or Formula 2 in a therapeutically effective amount with one or more nontoxic and pharmaceutically acceptable carrier, adjuvant or diluent, or other active ingredient. The composition of the present invention may be formulated in the forms of solution, suspension or emulsifier in the oily or aqueous medium, including an oral dosage form, or used in the form of dried powder to be dissolved in sterile or pyrogen-free water for parenteral use such as s.c., i.v., or i.m. injection.

The composition of the present invention may be formulated in the following oral dosage form according to the conventional method, using pharmaceutically acceptable carriers and excipients: tablet, troche, sugar-coated tablet, aqueous or oily suspension, dispersible powder or particle, emulsifying solution, soft or hard capsule, syrup or elixir. The above dosage forms may be formulated according to unit, dosing or type.

Among the above oral dosage form, tablets cotain the active ingredient in admixture with non-toxic pharmaceutically acceptable excipients which are suitable for the manufacture of tablets. These excipients may be for example, inert diluents such as calcium carbonate, sodium carbonate, lactose, calcium phosphate or sodium phosphate etc.; granulating and disintegrating agents such as corn, starch or alginic acid etc.; binding agents such as starch, gelatin or acacia etc.; and lubricating agents such as magnesium stearate, stearic acid or talc etc. The tablets may be uncoated or they coated by known techniques to delay disintegration and absorption in the gastrointestinal tract. For example, a time delay material such as glyceryl monostearate or glyceryl distearate may be employed. Formulation for oral use may also be presented as hard gelatin capsules wherein the active ingredient is mixed with an inert solid diluent for example calcium carbonate, calcium phosphate or kaolin; or as soft gelatin capsules wherein the active ingredient is mixed with water or an oil medium for example peanut oil, liquid paraffin or olive oil.

Aqueous suspensions contain the active materials in admixture with excipients suitable for the manufacture of aqueous suspensions. Such excipients are suspending agents such as sodium carboxymethylcellulose, methylcellulose, hydropropylmethylcellulose, sodium alginate, polyvinylpyrrolidone, gum tragacanth and gum acacia etc.; dispersing or wetting agents; phosphatide such as lecithin; condensation products of an alkylene oxide with fatty acids such as polyoxyethylene stearate; condensation products of alkylene oxide with long chain aliphatic alcohols such as heptadecaethyleneoxycetanol; condensation products of ethylene oxide with partial esters derived from fatty acids and hexitol anhydride such as polyethylene sorbitan monooleate. The aqueous suspensions may also contain one or more preservatives, coloring agents, flavoring agents or sweetening agent.

Oily suspensions may be formulated by suspending the active ingredients in a vegetable oil such as olive oil, sesame oil etc. or in a mineral oil such as liquid paraffin. The oily suspensions may contain a thickening agent such as beeswax, hard paraffin or cetyl alcohol. Further, preservatives, coloring agents, flavoring agents or sweetening agent may be added thereto, and these compositions may be preserved by the addition of an anti-oxidant such as ascorbic acid.

Dispersible powders and granules contains the active ingredient in admixture with a dispersing or wetting agent, suspending agent and one or more preservatives. Suitable dispersing or wetting agents and suspending agents are exemplified by those already mentioned above. Additional excipients such as sweetening, flavoring and coloring agents may also be present.

Pharmaceutical composition of the present invention may also be in the form of oil-in-water emulsions. The oily phase may be a vegetable oil such as olive oil or a mineral oil such as liquid paraffin, etc. Suitable emulsifying agents may be naturally-occurring phosphatides such as soy bean lecithin, and esters or partial esters derived from fatty acids and hexitol anhydrides such as sorbitan monooleate, and condensation products of the said partial esters with ethylene oxide such as polyoxyethylene sorbitol monooleate.

Syrups and elixirs may be formulated by mixing the active ingredients with sweetening agent such as glycerol propylene glycol, sorbitol or sucrose etc.

The parenteral dosage form may be applied by formulating some types of sterile injectable solution or suspension mixing the active ingredients with non-toxic diluent or solvent such as 1,3-butanediol. The commercially available excipient or solvent may include water, Ringer's solution, and isotropic saline solution, as well as ethanol and co-solvents such as polyethylene glycol and polypropylene glycol. Further, the sterile, non-volatile oil may be conventionally used as solvent or suspension solvent. The bland fixed oil added for this object comprises synthetic mono-, di-glyceride. Further, aliphatic acid such as oleic acid may be used for the preparation of injection composition.

The suppository dosage form for rectum use may be formulated in a mixing form with adequate, non-irritant types of excipient such as cocoa butter, polyethylene glycol, in a manner such that a drug is in a solid form at room temperature but it turns into liquid at the temperature of rectum, thus releasing the drug in a dissolved form.

When the composition of the present invention is administered for the treatment of disease, the dosing of the active ingredient compound may vary depending on age, body weight, general health conditions, sex, meals, administration time, excretion rate, concurrent drugs, and severity of disease during treatment. However, in case when the powder of Tochu-kaso J300 is used, the dosing of Tochu-kaso J300 may be daily administered 1~3 g per patient with 60 kg of body weight. According to the present invention, the mixing ratio of the compound of the present invention and carriers for the formulation of one dosage form may vary depending on route of administration and patient, respectively.

Food composition for treating AIDS comprising 3-[5-(methoxy-ethyl)-3,6-dioxo-piperazine-2-yl]propionic acid and 4-methyl-2-[(pyrolidine-2-carbonyl)-2-amino]pentanoic acid as a food additive can be easily formulated by one skilled in the art without limitation in the formation including drink etc.

The present invention will be described in more detail by way of the following examples. However, the scope of the present invention is not limited by the following examples.

PREFERRED EMBODIMENT OF THE INVENTION

Example 1

Comparison of the Anti-HIV Activities of the Extracts of the Tochu-Kaso

First, to confirm the anti-HIV activity of the extracts of the Tochu-kaso J300, the activities of the water extract and methanol extract of the Tochu-kaso J300 were compared.

Water extract of Tochu-kaso J300 was prepared by boiling the Tochu-kaso J300 powder in the water then filtering out the residue to obtain water fraction. Methanol extract of Tochu-kaso J300 was prepared with the same method above by using methanol as a solvent for extract.

The results are explained with reference to the figures.

In FIGS. 2 to 8, 11 and 18, the term "Infected" (diamond mark ♦) is for the samples that a reagent is applied after the cells are infected with the virus to observe the protection of cells from the cell destruction of HIV. The term "Uninfected" (square mark ☐) is for the samples that only reagent is added with different concentration to observe the toxicity of the reagent according to the concentration. Further, X axis represents the concentration of the sample and Y axis represents the survivability of the cells in percentages (%).

Figure 2:
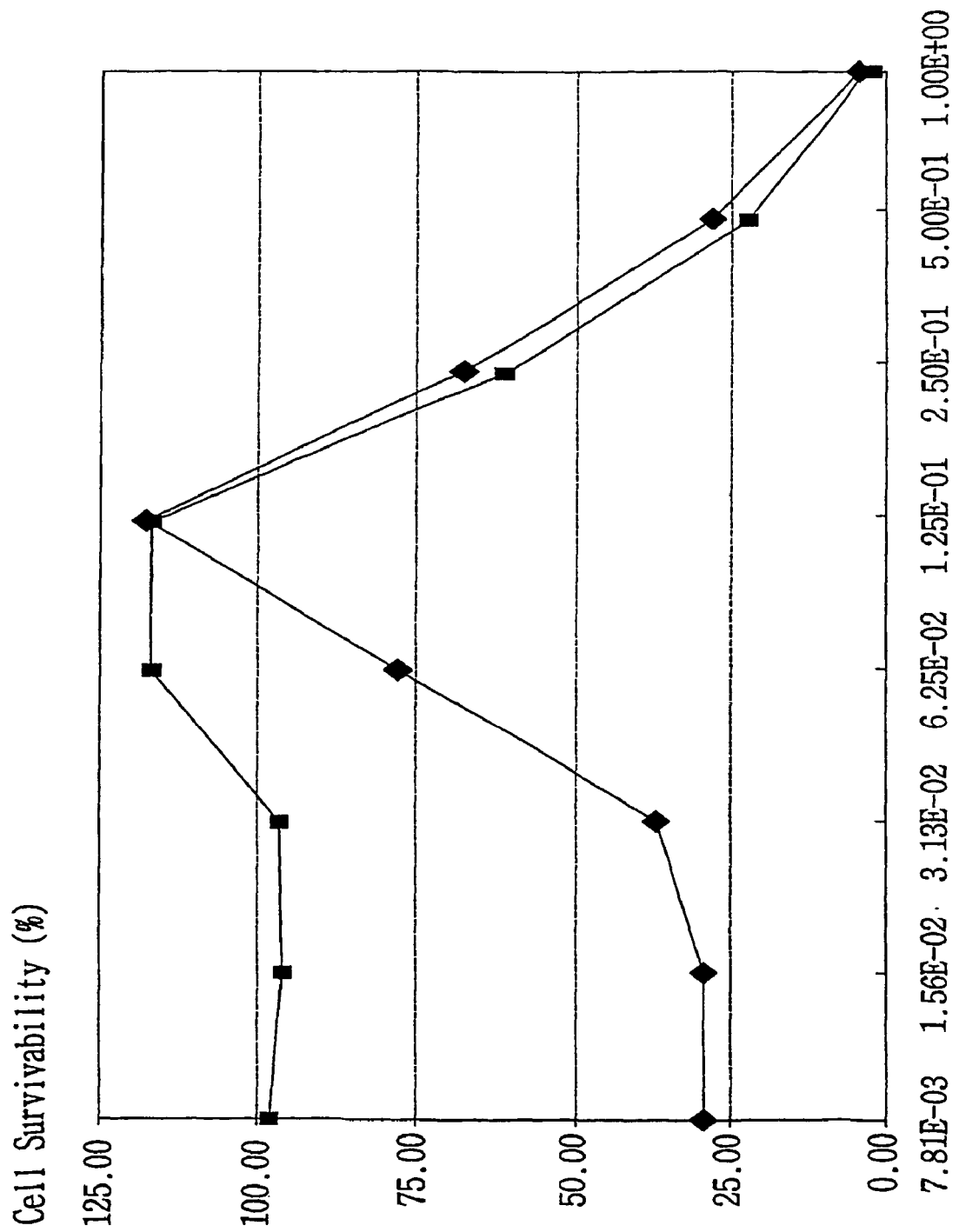
FIG. 2 shows the activity of aqueous extract of the Tochu-kaso J300 (J300W) inhibiting the HIV activity.

FIG. 2 shows the anti-HIV activity of aqueous extract of the Tochu-kaso J300 (J300W), which indicates that an anti-HIV component exists therein. That is, as the concentration of the aqueous extract of the Tochu-kaso J300 increases, the anti-HIV activity increases. However, at the concentration more than $1.25 \times 10^{-1}$, both "Infected" and "Uninfected" decrease, which shows that cell toxicity appears in those concentrations.

Figure 3:
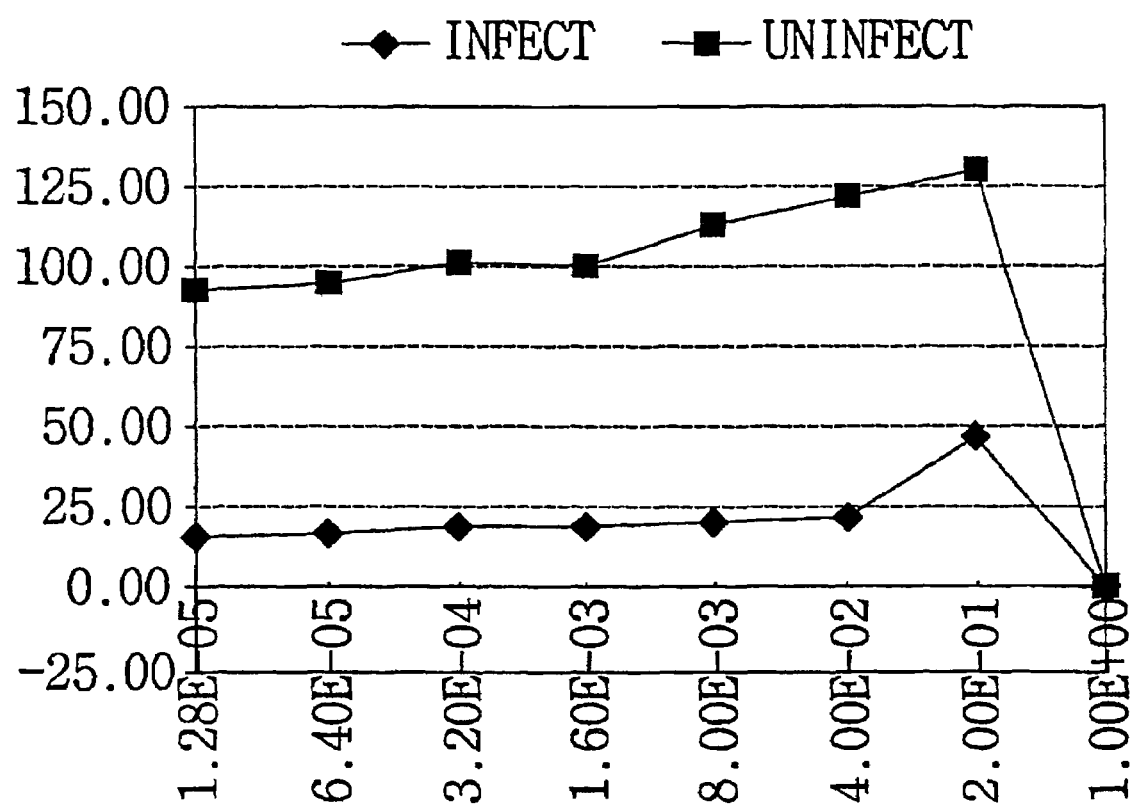
FIG. 3 shows the activity of methanol extract of the Tochu-kaso J300 inhibiting the HIV activity.

FIG. 3 shows the anti-HIV activity of methanol extract of the Tochu-kaso J300, and it can be seen that although the concentration of the methanol extract of the Tochu-kaso J300 increases, the anti-HIV activity is not changed. Compared with FIG. 2 that shows the anti-HIV activity, although the concentration of the sample is increased, cells are not protected. Therefore, this fraction is regarded as not having anti-HIV activity.

Figure 4:
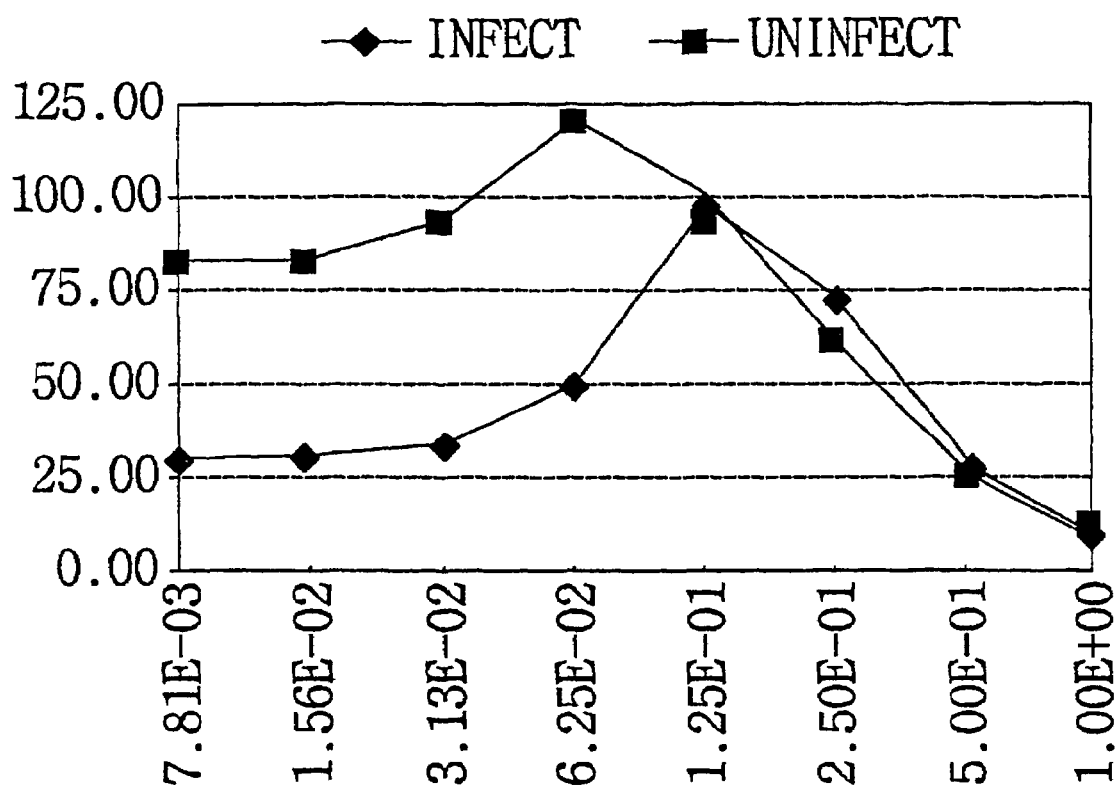
FIG. 4 shows the activity of protein-free layer from the aq. extract of the Tochu-kaso J300 inhibiting the HIV activity.

On the other hand, FIG. 4 shows the anti-HIV activity of protein-free layer of the aqueous extract of the Tochu-kaso J300, which shows that protein-free fraction has a good anti-HIV activity.

Figure 5:
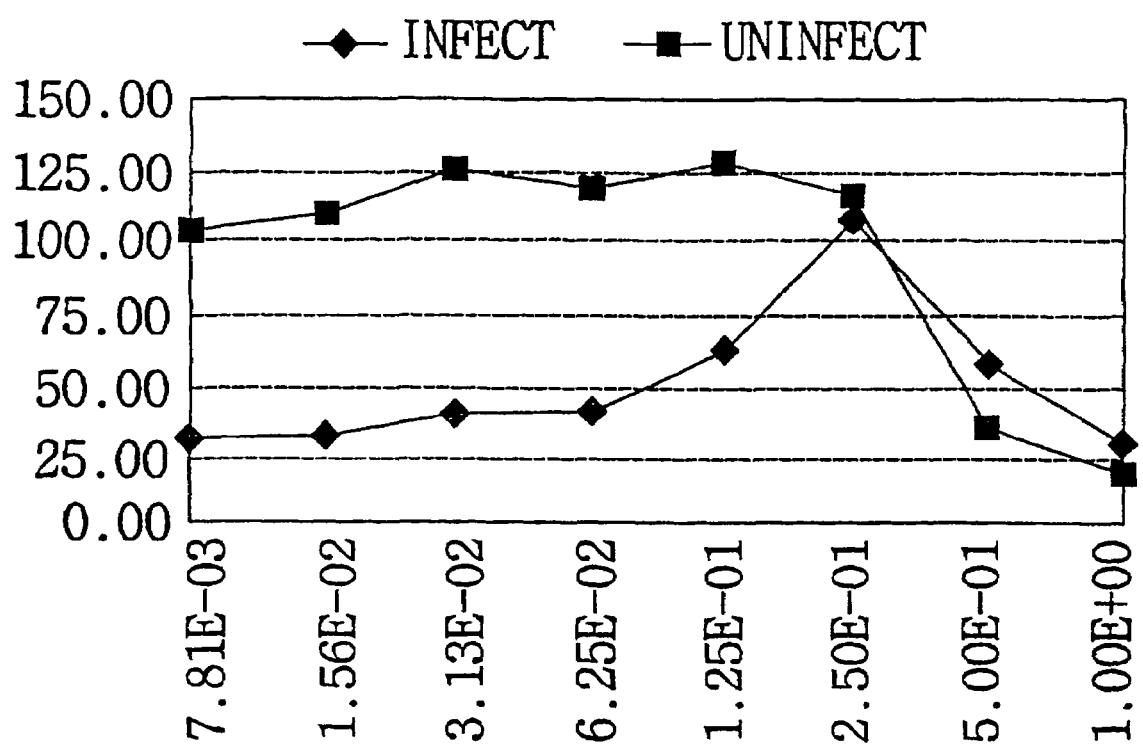
FIG. 5 shows the activity of the fraction having 1,000 D or less of molecular weight from the aq. extract of the Tochu-kaso J300 inhibiting the HIV activity.
Figure 6:
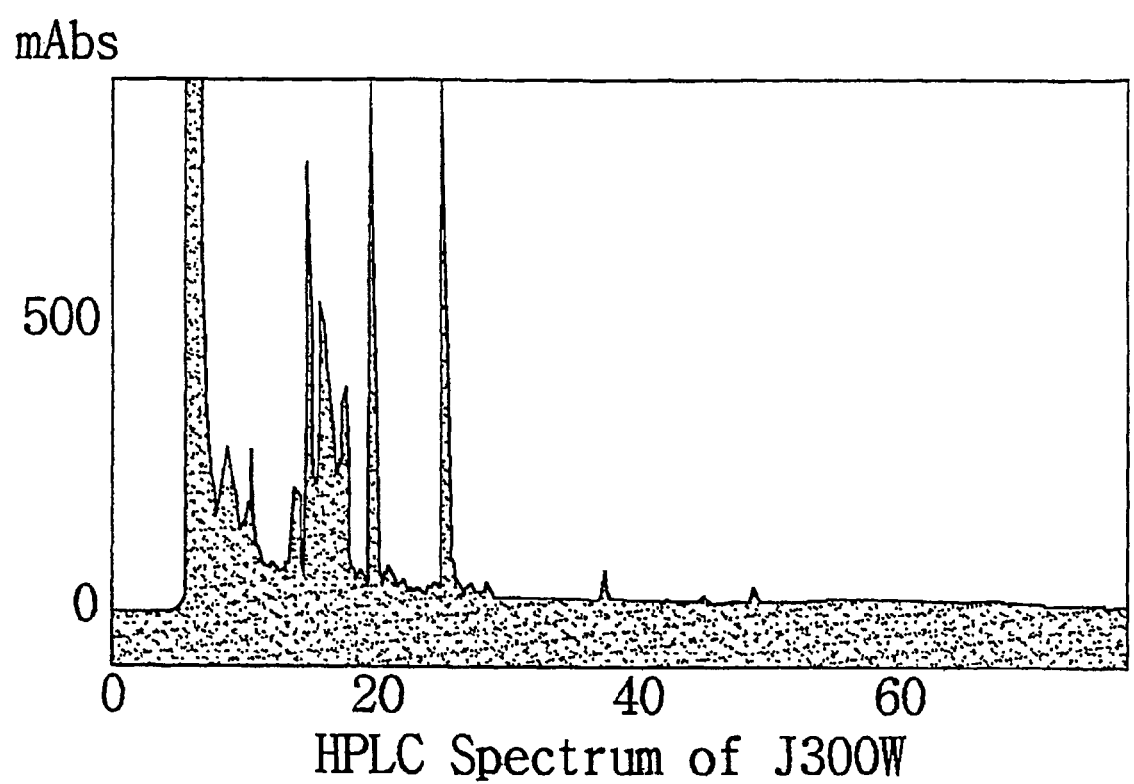
FIG. 6 shows the HPLC (High Performance Liquid Chromatography) spectrum of aq. extract of the Tochu-kaso J300 inhibiting the HIV activity.

FIG. 5 shows the anti-HIV activity of the fraction having 1,000 D or less of molecular weight from the aqueous extract of the Tochu-kaso J300, and favorable anti-HIV activity is shown in that fraction.

Example 2

Separation and Purification of the Active Component From the Extracts of the Tochu-Kaso J300

Figure 1:
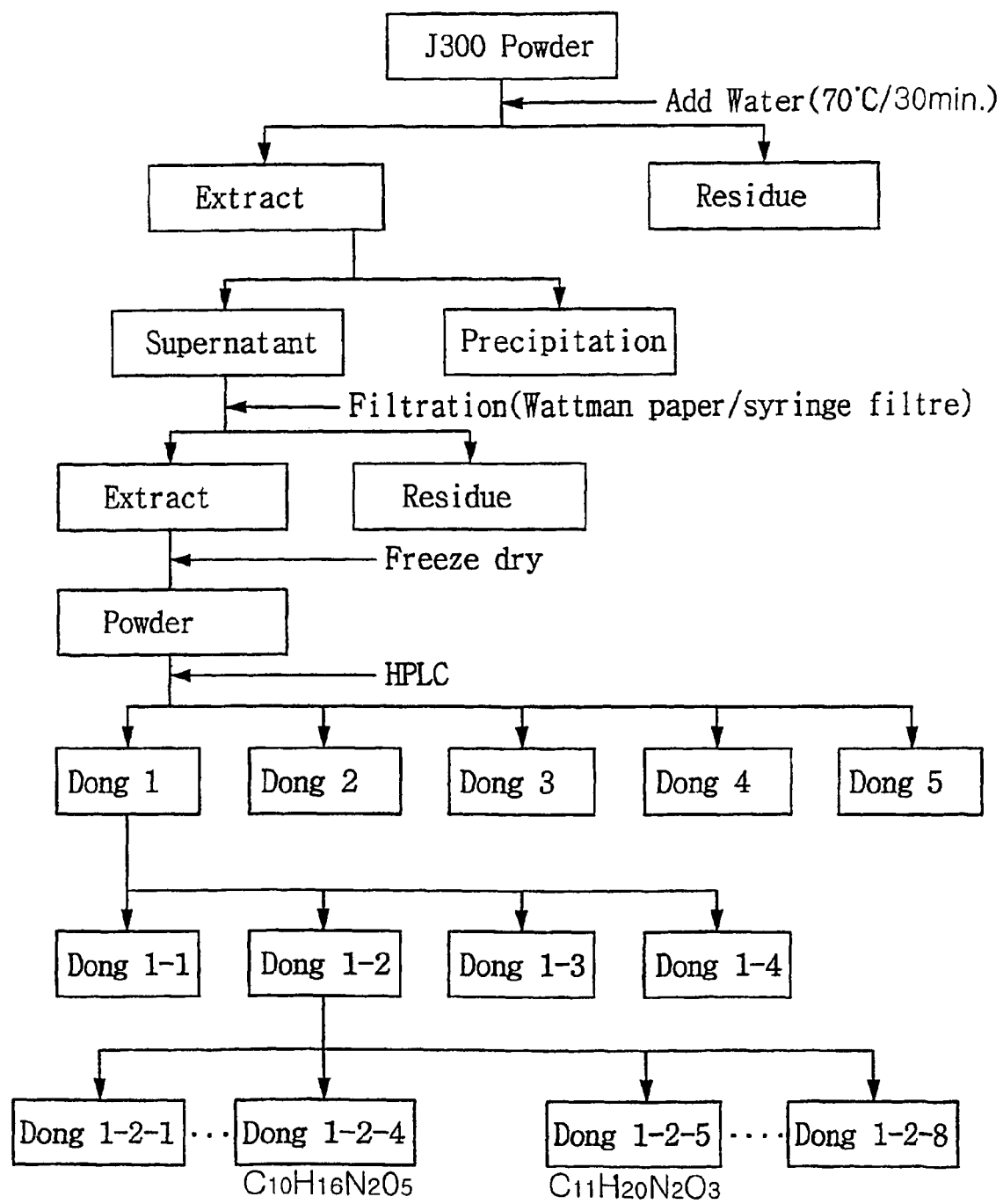
FIG. 1 shows the process for separating and purifying the active fraction of Tochu-kaso J300, Dong 1-2-4, {3-[5-(methoxy-ethyl)-3,6-dioxo-piperazine-2-yl]propionic acid} and Dong 1-2-5, {4-methyl-2-[(pyrolidine-2-carbonyl)-2-amino] pentanoic acid}.

The method for separating and purifying the active component from the Tochu-kaso J300 is described with reference to FIG. 1.

1) Powdered Tochu-kaso J300 was boiled in the water at 70° C. for 30 minutes and the aqueous layer is obtained, and the aqueous layer (aq. fraction) is evaporated and freeze dried to obtain crude extract of Tochu-kaso J300. Using 2.63 g of the above crude extract of Tochu-kaso J300 performed HP 20 adsorption chromatography.

As elution solvents, 100% distilled water, 50% aq. MeOH, 50% aq. acetone, 100% MeOH, 100% acetone were used orderly, and 50% aq. MeOH and 50% aq. acetone were used with two fractions. HPLC was repeatedly performed for each fraction to scan anti-HIV activity.

Each extract from each elution obtained after removing the solvent was designated as Dong 1 to 7, and the weights were respectively, 2.55 g (Dong 1), 0.390 g (Dong 2), 0.044 g (Dong 3), 0.030 g (Dong 4). 0.015 g (Dong 5), 0.004 g (Dong 6), 0.003 g (Dong 7).

2) Among the above fractions, Dong 1 again underwent HPLC with the same order above to observe anti-AIDS activity. As the result, Dong 1-1 and Dong 1-2 expressed intense activity, and the activity of Dong 1-2 is about 1000 times more intense than Dong 1-1.

Further, Dong 1-2 was again performed HPLC with active carbon wherein the elution solvents were similarly 100% distilled water, 50% aq. MeOH, 50% aq. aceton, 100% MeOH. The products obtained after removing the solvent were designated as Dong 1-2-1 to 1-2-8 respectively. The amounts of Dong 1-2-1, 4, 5 and 8 were 0.446 g (Dong 1-2-1), 0.469 g (Dong 1-2-4), 0.190 g (Dong 1-2-5) and 0.006 g (Dong 1-2-8), respectively. Theses fractions are again underwent anti-AIDS activity measurement, and found that Dong 1-2-4 and Dong 1-2-5 have more intense activity compared to others.

3) 100% distilled water fraction of active carbon chromatography (Dong 1) was dissolved in 35% aq. acetonytrile, then HPLC (YMC amino column, 2×25 cm, 2 ml/min, MeOH) separation was performed to obtain each amount of products of 9.9, 2.8, 10.9, 7.7, 32.7, 10.3, 21.4 and 13.7 mg at each retension time (Rt) of 10, 12, 14, 15, 18, 22, 29 minutes and residue respectively. In the peak of Rt 10 minute, there are glutamic acid as main component and a little amount of threonine. In the peak of Rt 12 minute, there are glutamic acid and threonine. In the peak of Rt 14 minute, the OH group of threonine is converted to methoxy group. In the peak of Rt 15 minute, there are proline as main component and a little amount of a compound that the OH group of threonine is converted to methoxy group and glutamic acid. In the peak of Rt 18 minute, there are arginine as main component and a little amount of glutamic acid and unknown material. The peak of Rt 22 minute indicates alanine. In the peak of Rt 29 minute, there is a compound that the carboxyl group distant from amino group is esterified.

Continuously, 50% aq. MeOH fraction of active carbon chromatography (Dong 1-2) was dissolved in 40% aq. acetonitrile, then HPLC(YMC amino column, 2×25 cm, 2 ml/min, MeOH) separation was performed. 21.6, 36.6, 93.6 mg of products were obtained at each retention time of 13, 13.5, 14.5 minutes respectively. The peak of Rt 13 minute indicates dipeptide of proline and leucine, that is, leucylproline; the peak of Rt 13.5 minute indicates glycerol; and the peak of Rt 14.5 seems to be derivatives of sugar.

Finally, 50% aq. MeOH fraction (Dong 1-2) obtained from the separation with HP 20 adsorption chromatography is dissolved 25% aq. acetonitrile, then HPLC(YMC amino column, 2×25 cm, RI measurement, 2 ml/min) separation was performed. 2.4, 3.2, 5.0, 3.1, 7.2, 14.9, 6.7 mg of products were obtained at each retention time of 8, 10, 12, 19, 26, 32, 36 minutes respectively. According to 1H NMR analysis, the peak of Rt 10 minute seems to be a mixture of deoxyadenosine and thymidine with a ratio of 3:2, and the peaks of Rt 12, 19, 26, 32 and 36 minutes are determined to be adenosine, uridine, tryptophane, phenylalanine and guanotidine. 207.4 mg of residue that is not identified from HPLC is also obtained. Further, a little amount of two other substitutes of amino acid was found from NMR analysis.

4) The fraction of Rt 19 minute was proved to be dipeptide derivative of glutamic acid and treonine (GT: Dong 1-2-4). To clarify the chemical structure of the active component NMR analysis was performed. $^1$H(Proton), Cosy45, $^{13}$C, DEPT, HSQC, HMBC was adopted to analyze the structure. The results of the analysis are shown in FIGS. 12 to 17. From the NMR analysis, the compound of the fraction was proved to be 3-[5-(methoxy-ethyl)-3,6-dioxo-piperazine-2-yl]propionic acid. $^1$H NMR data (ppm); δ 1.2 (d, 3H), δ2.0 (m, 2H), δ2.3 (m, 2H), δ3.0 (s, 3H), 3.2 (m, 1H), δ3.5 (m, 1H), δ3.65 (m, 1H): $^{13}$C NMR data (ppm); δ13, 27, 33, 55, 60.5, 60.6, 66, 170, 174, 180.

On the other hand, the fraction of Rt 26 minutes was proved to be dipeptide derivative of leucine and proline (LP: Dong 1-2-5), same analysis was performed as done above. The results of the analysis are shown in FIGS. 19 to 24, and from the results of NMR analysis, the fraction was proved to be 4-methyl-2-[(pyrolidine-2-carbonyl)-2-amino]pentanoic acid. $^1$H NMR data (ppm); δ 0.86 (d, 6H), δ 1.55 (m, 2H), δ 1.6 (m, 1H), δ 1.9 (m, 2H), δ 3.2 (m, 2H), 3.3 (m, 2H), 3.5 (m, 1H), 4.0 (m, 1H): $^{13}$C NMR data (ppm): δ 10, 20, 23.8, 29, 40, 46, 54, 61.5, 63.2, 172, 173

Example 3

Anti-HIV Activity of Tochu-Kaso J300

1. Stability of the Active Compound

Finding the most suitable condition that maintains the activity of a material is very important factor in the process of separation and identification of an active material. Therefore, the degree of activity was measured in various temperatures and preservation time to find out a suitable condition. In the present invention, the active compound obtained above was preserved for 1 week at the temperatures of −20° C., 4° C., 22° C. and 37° C., and no deterioration was found. It shows that the extracts above are very stable compounds.

2. Measurement of Anti-HIV Activity

In the present invention, the measurement of anti-HIV activity followed the method of National Cancer Institute (U.S.A.). In the method, survivability of cells that are protected from the destruction due to HIV was measured when the cells were treated with the active component of the present invention to determine the anti-HIV activity of the material.

In detail, the mixture of cell+HIV+sample (active compound) was cultured for 1 week, and then cell toxicity was measured by XTT method. In each measurement, the following control samples were used to determine the activity of Tochu-kaso J300 fractions.

(1) A control sample cultured only with cells: this is a positive control, and the survivability of this sample was designated to be 100%.

(2) Cell+HIV: this is a negative control, and most of the cells are destructed by HIV. The survivability of this sample was designated to be 0%.

(3) Cell+samples with different concentration of extract: this is to measure the toxicity to the cell.

(4) Samples with different concentration of extract only: this is to measure the background color due to the samples themselves.

(5) Cell+HIV+AZT: because AZT is well-known ant-HIV active material, a formal pattern is expected in the graph. By comparing the pattern of the graph, the suitability of the conditions of the examples is affirmed.

The viruses used in the example are mutant viruses wherein tat and rev that are important gene of onset of HIV are modified, and treated to produce mutant product thereof in the host cell. With this treatment, the HIV was modified to propagate in a specific host cell only, but not able to propagate in general cell, which increases safety.

In this example, colorimetric assay was adopted to observe the growth and death of the cells, which uses the fact that tetrazole salt (MTT, XTT, WST-1) is broken only in the living cell to form non-soluble formazan structure. By quantitating the amount of the formazane wih ELISA method, the amount of living cell is measured quantitatively.

Figure 11:
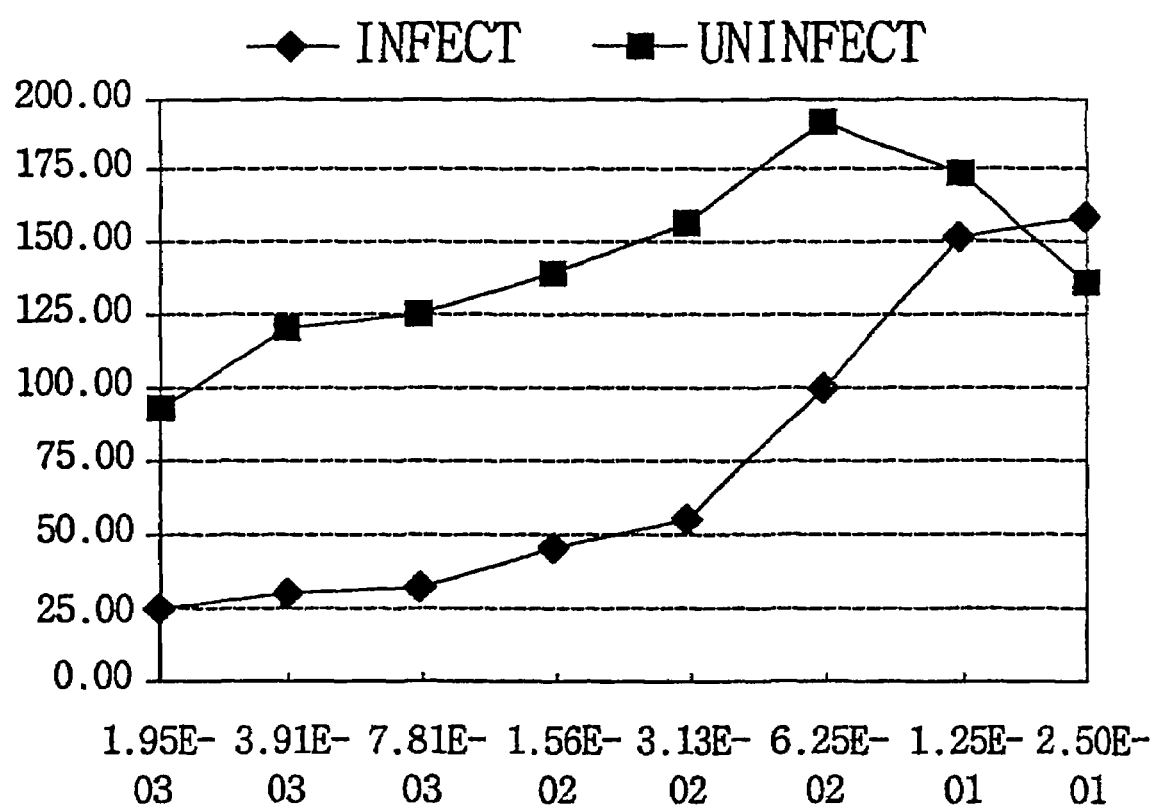
FIG. 11 shows the activity of the 3-[5-(methoxy-ethyl)-3, 6-dioxo-piperazine-2-yl]propionic acid inhibiting the HIV activity.
Figure 12:
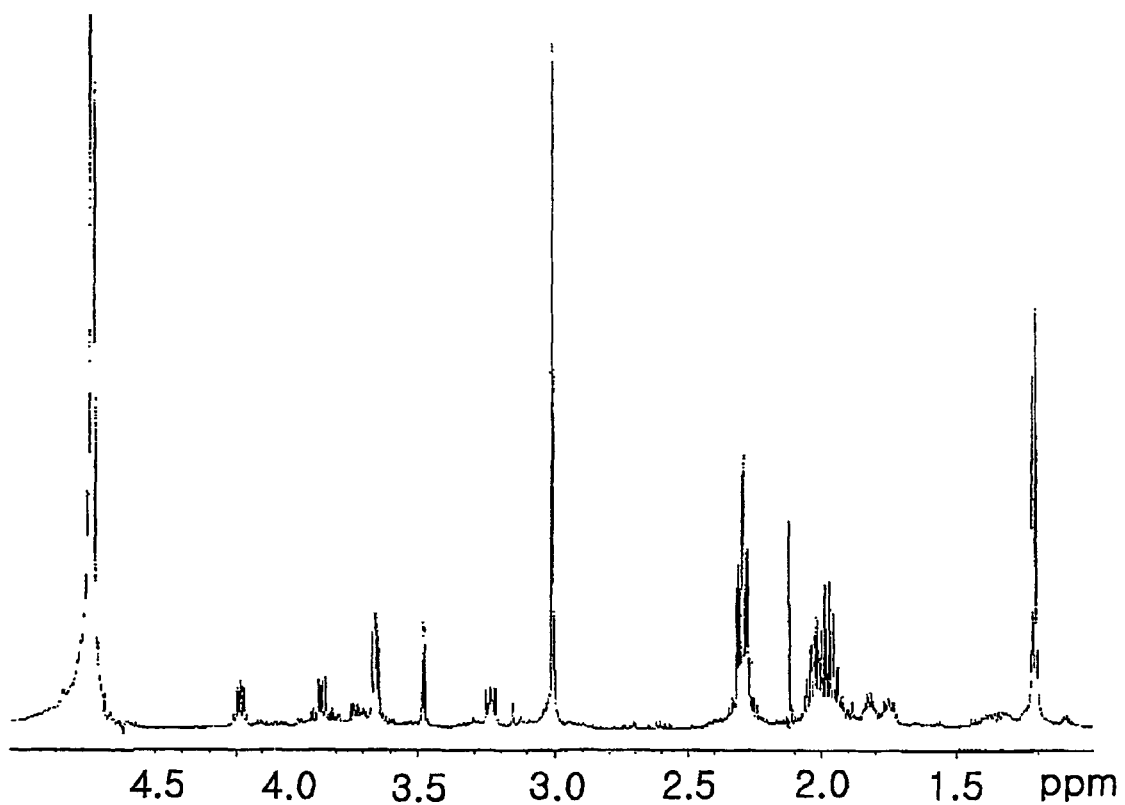
FIG. 12 is 1H NMR spectrum to identify the chemical structure of the active material from Dong 1-2-4 fraction of the aq. extract of the Tochu-kaso J300.
Figure 13:
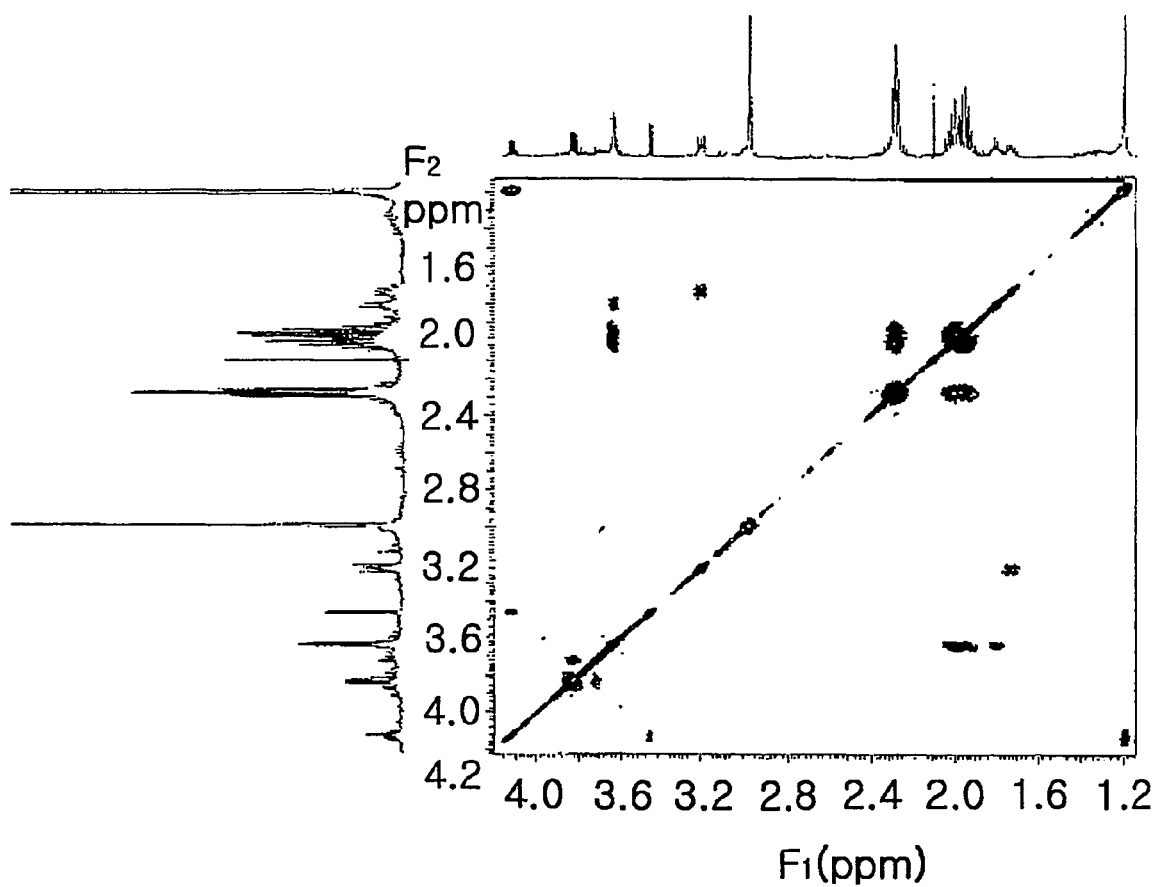
FIG. 13 is cosy 45 spectrum to identify the chemical structure of the active material from the Dong 1-2-4 fraction of the aq. extract of the Tochu-kaso J300.
Figure 14:
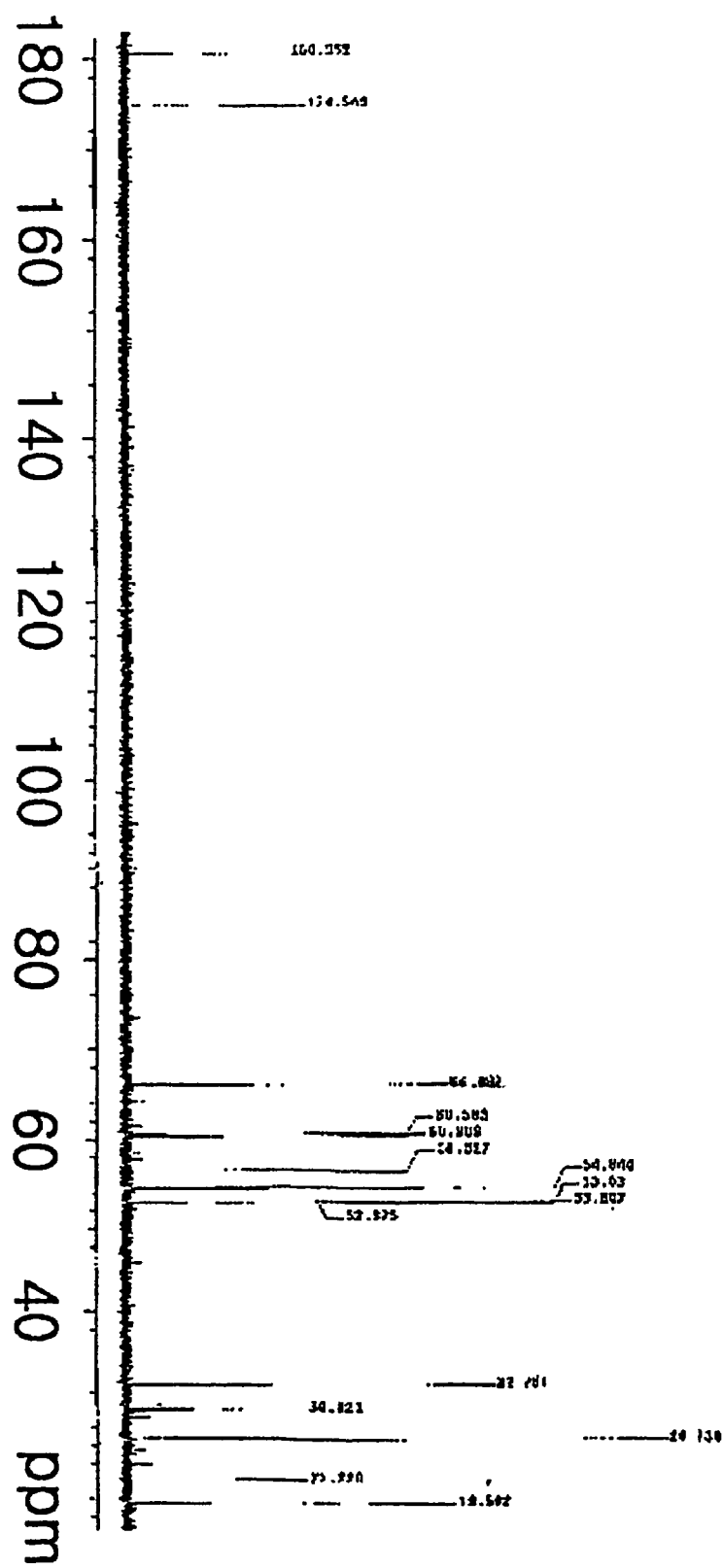
FIG. 14 is 13C NMR spectrum to identify the chemical structure of the active material from the Dong 1-2-4 fraction of the aq. extract of the Tochu-kaso J300.
Figure 15:
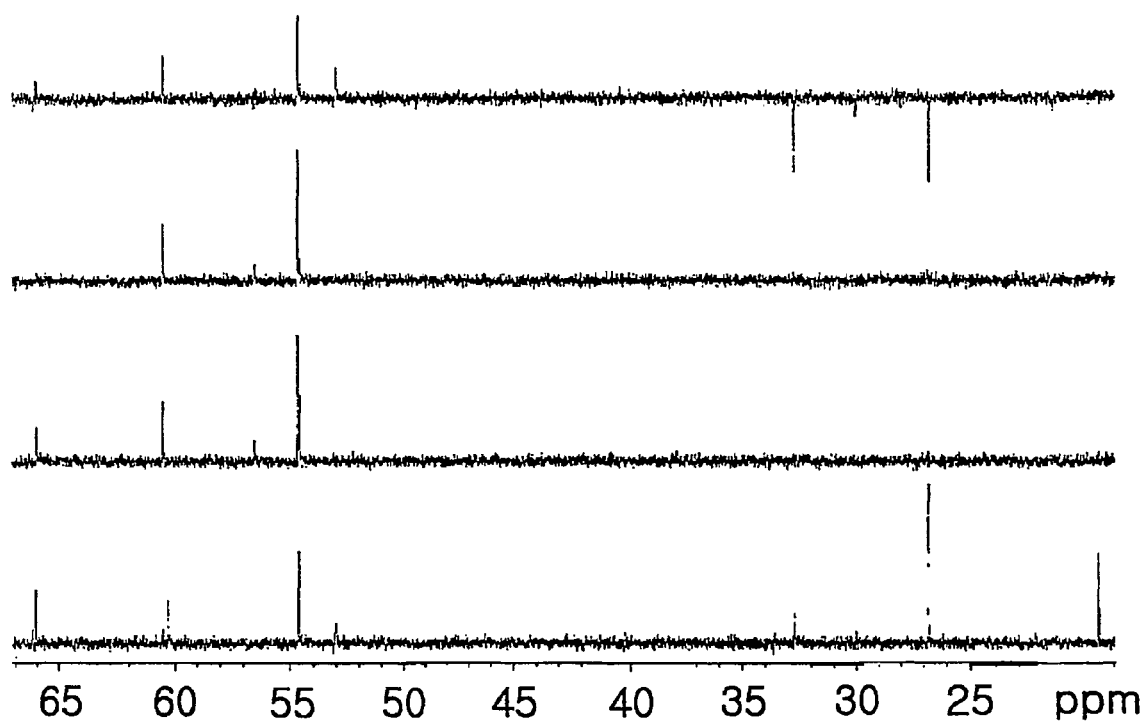
FIG. 15 is Dept spectrum to identify the chemical structure of the active material from the Dong 1-2-4 fraction of the aq. extract of the Tochu-kaso J300.
Figure 16:
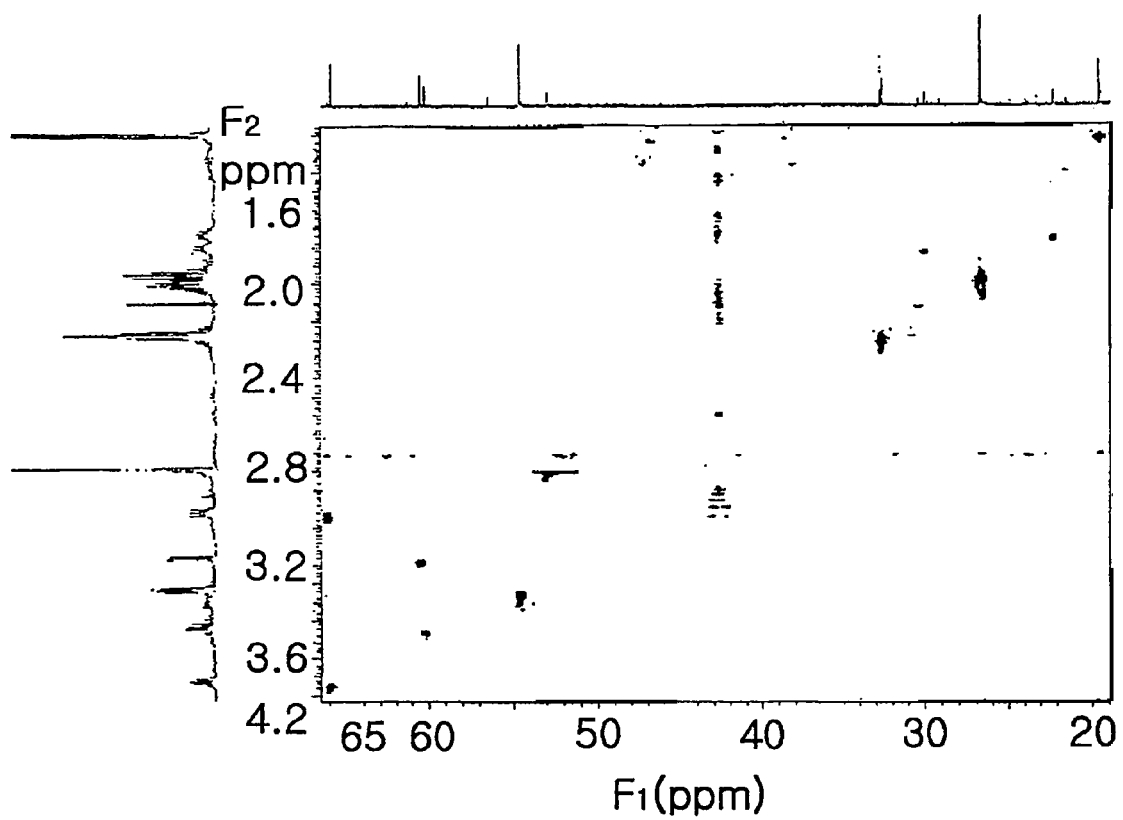
FIG. 16 is HSQC result to identify the chemical structure of the active material from the Dong 1-2-4 fraction of the aq. extract of the Tochu-kaso J300.
Figure 17:
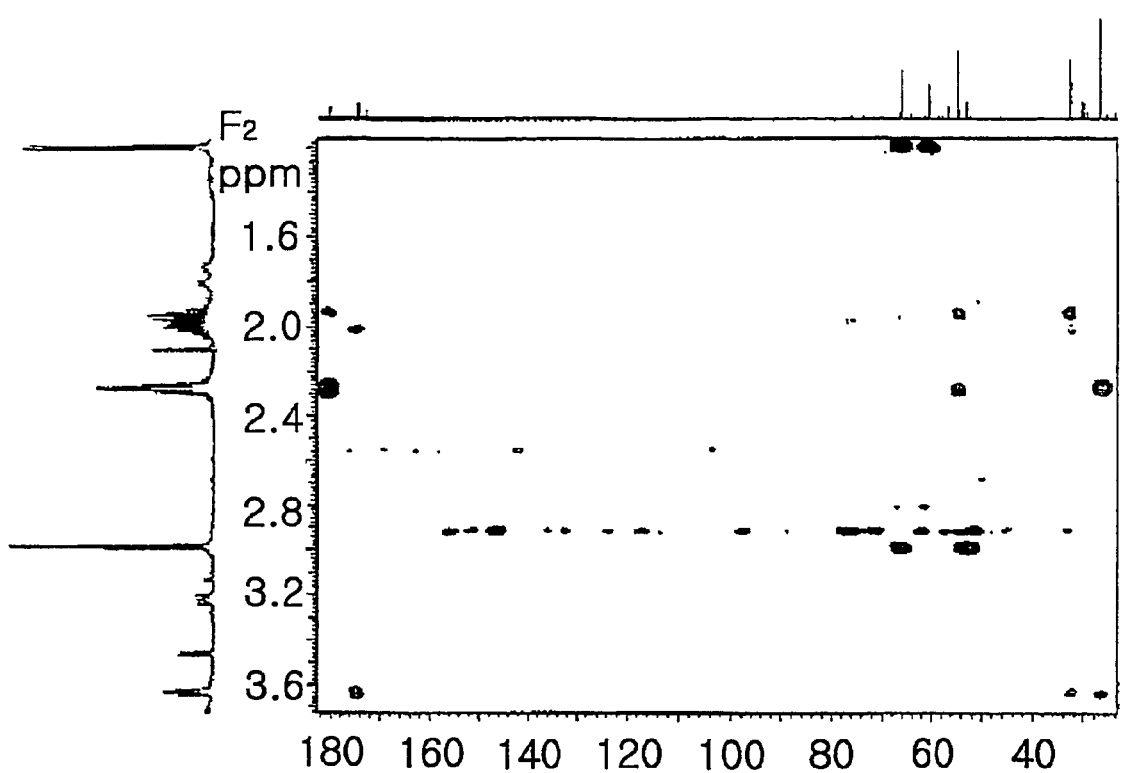
FIG. 17 is HMBC result to identify the chemical structure of the active material from the Dong 1-2-4 fraction of the aq. extract of the Tochu-kaso J300.
Figure 18:
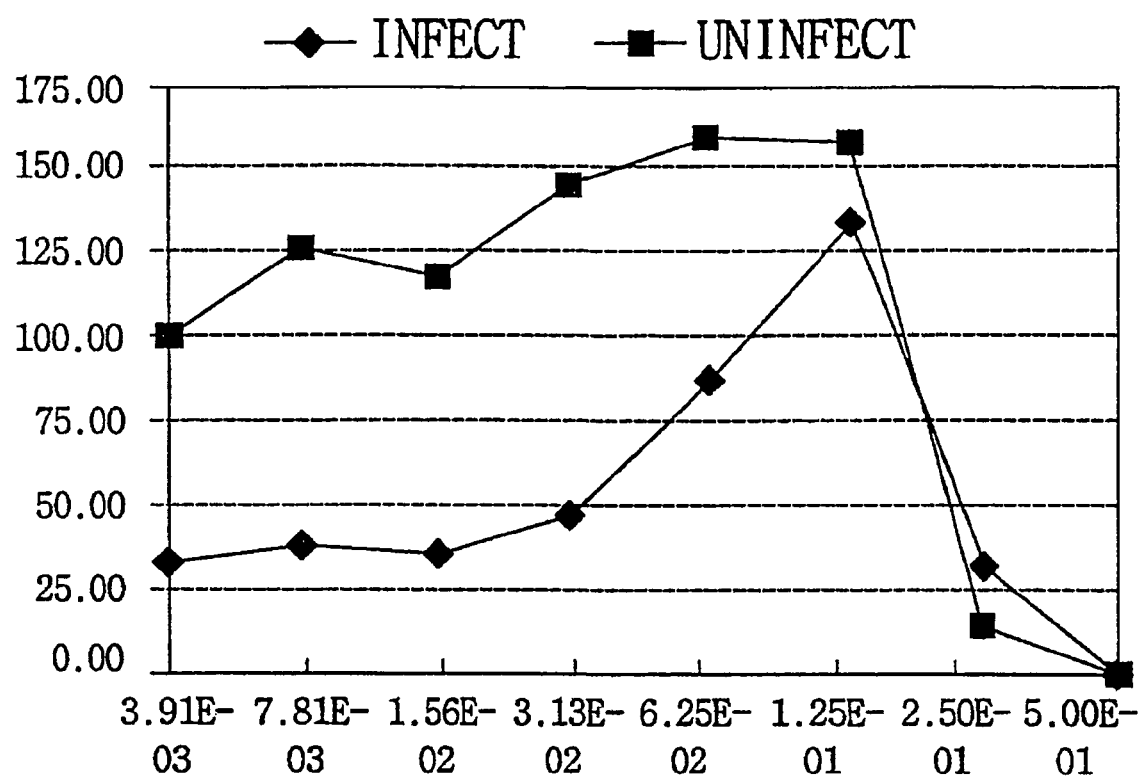
FIG. 18 shows the activity of the 4-methyl-2-[(pyrolidine-2-carbonyl)-2-amino]pentanoic acid inhibiting the HIV activity.
Figure 19:
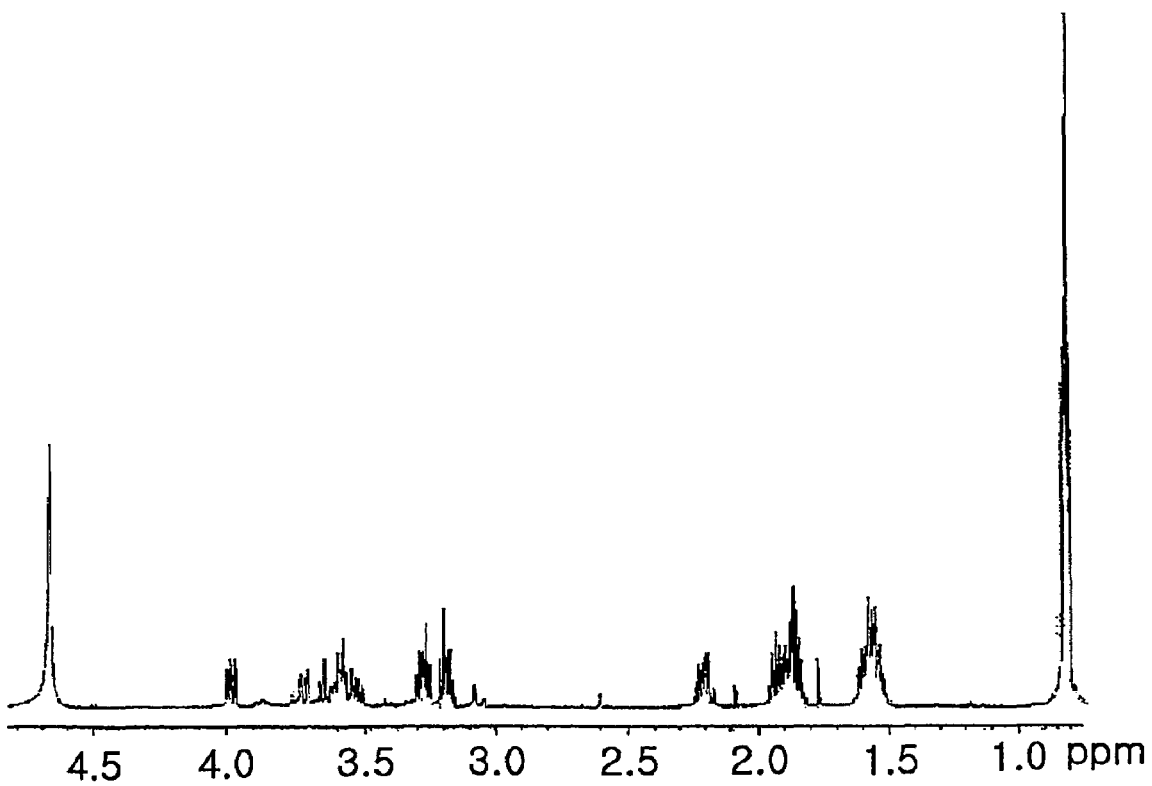
FIG. 19 is 1H NMR spectrum to identify the chemical structure of the active material from Dong 1-2-5 fraction of the aq. extract of the Tochu-kaso J300.
Figure 20:
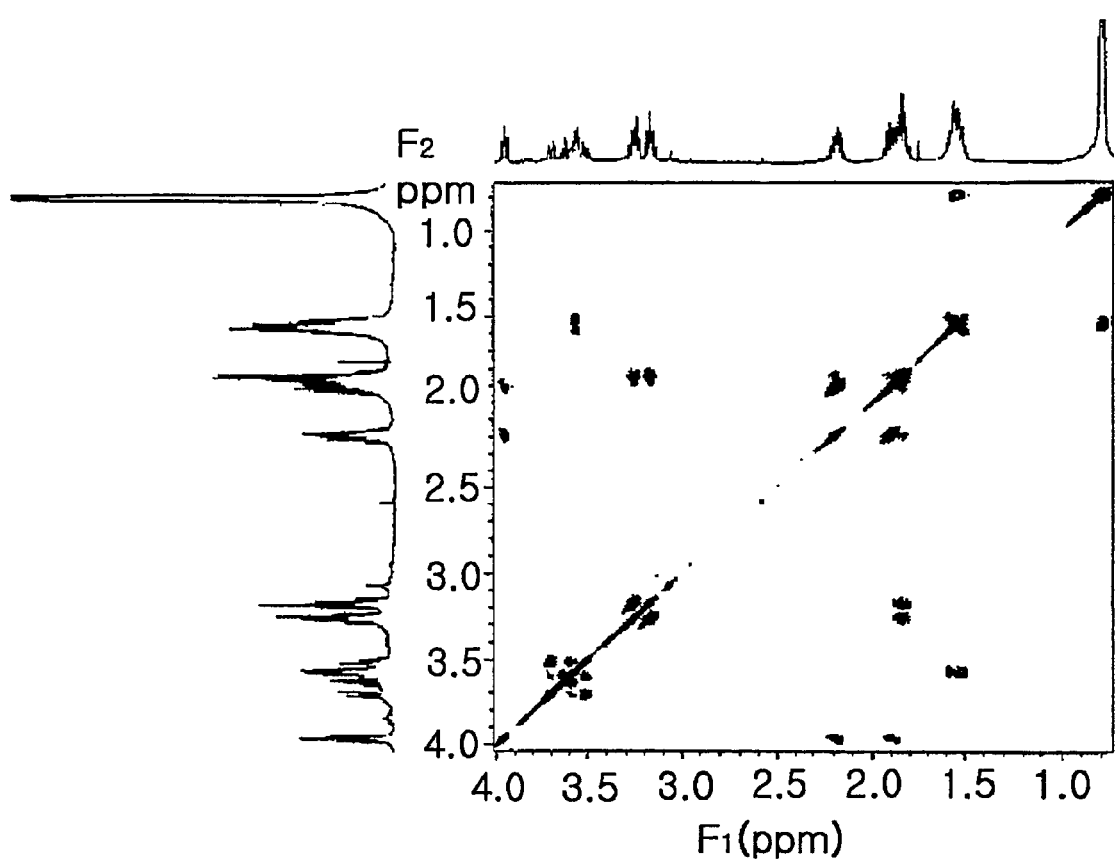
FIG. 20 is cosy 45 spectrums to identify the chemical structure of the active material from the Dong 1-2-5 fraction of the aq. extract of the Tochu-kaso J300.
Figure 21:
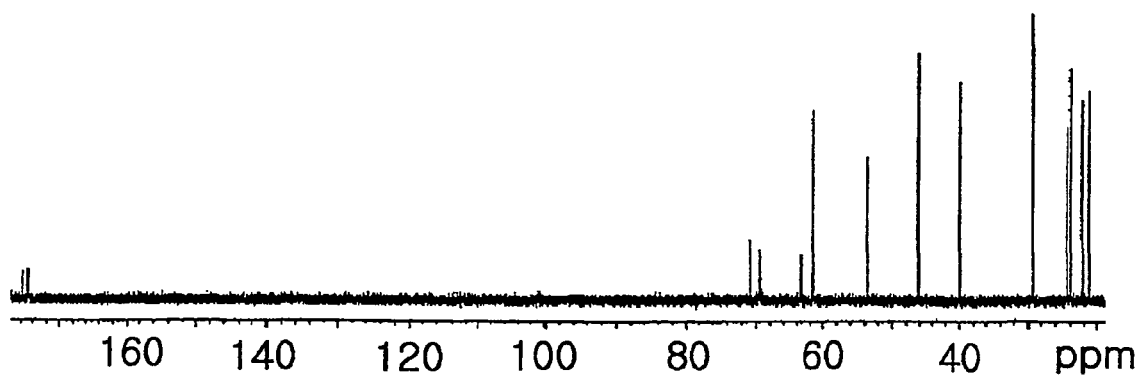
FIG. 21 is 13C NMR spectrum to identify the chemical structure of the active material from the Dong 1-2-5 fraction of the aq. extract of the Tochu-kaso J300.
Figure 22:
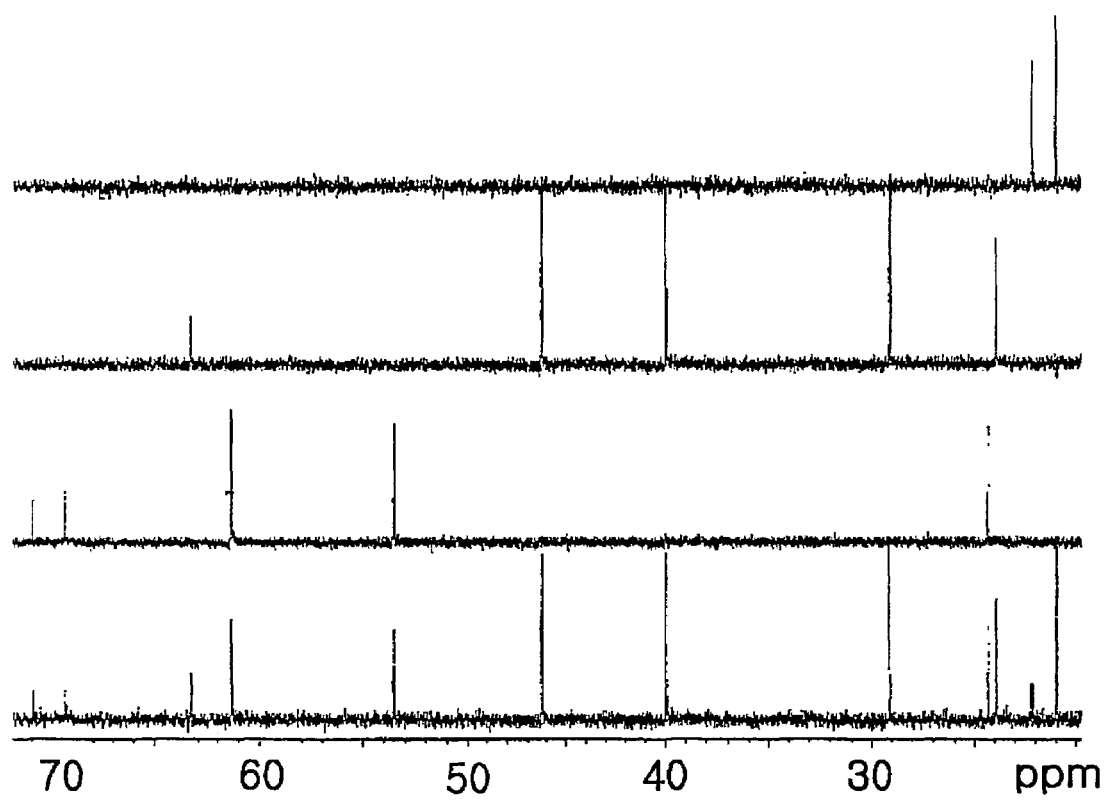
FIG. 22 is Dept spectrum to identify the chemical structure of the active material from the Dong 1-2-5 fraction of the aq. extract of the Tochu-kaso J300.
Figure 23:
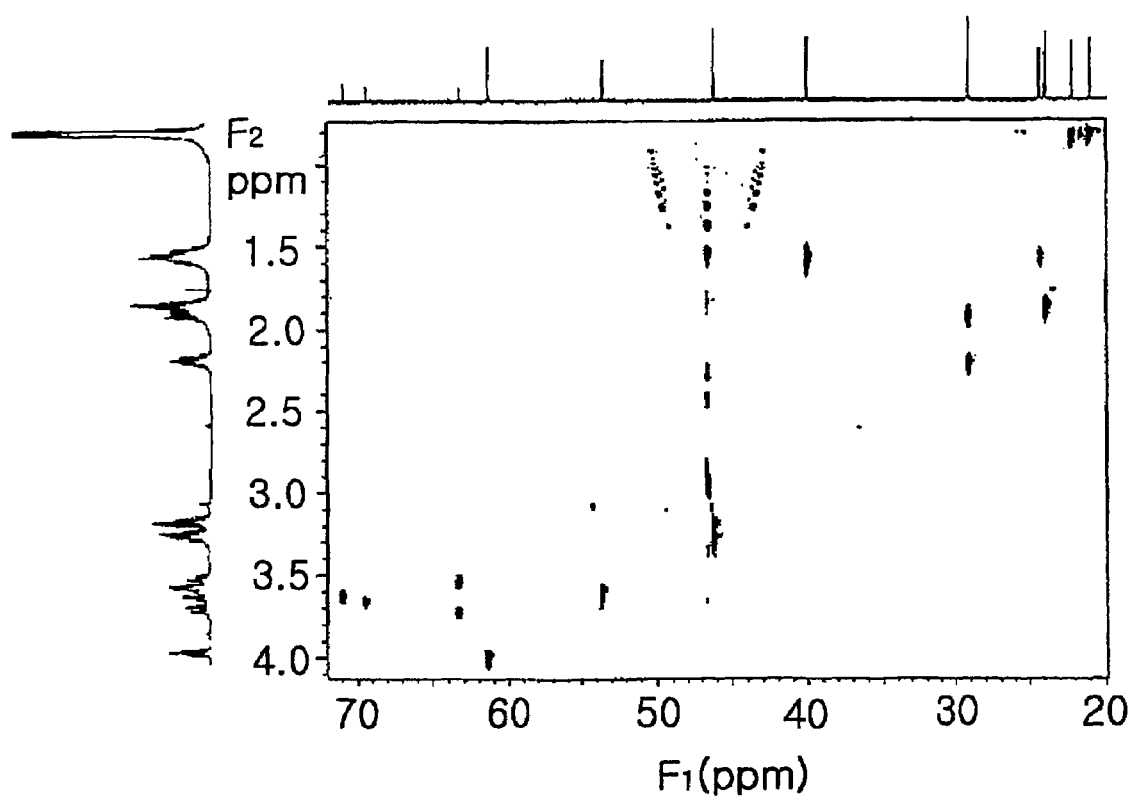
FIG. 23 is HSQC result to identify the chemical structure of the active material from the Dong 1-2-5 fraction of the aq. extract of the Tochu-kaso J300.
Figure 24:
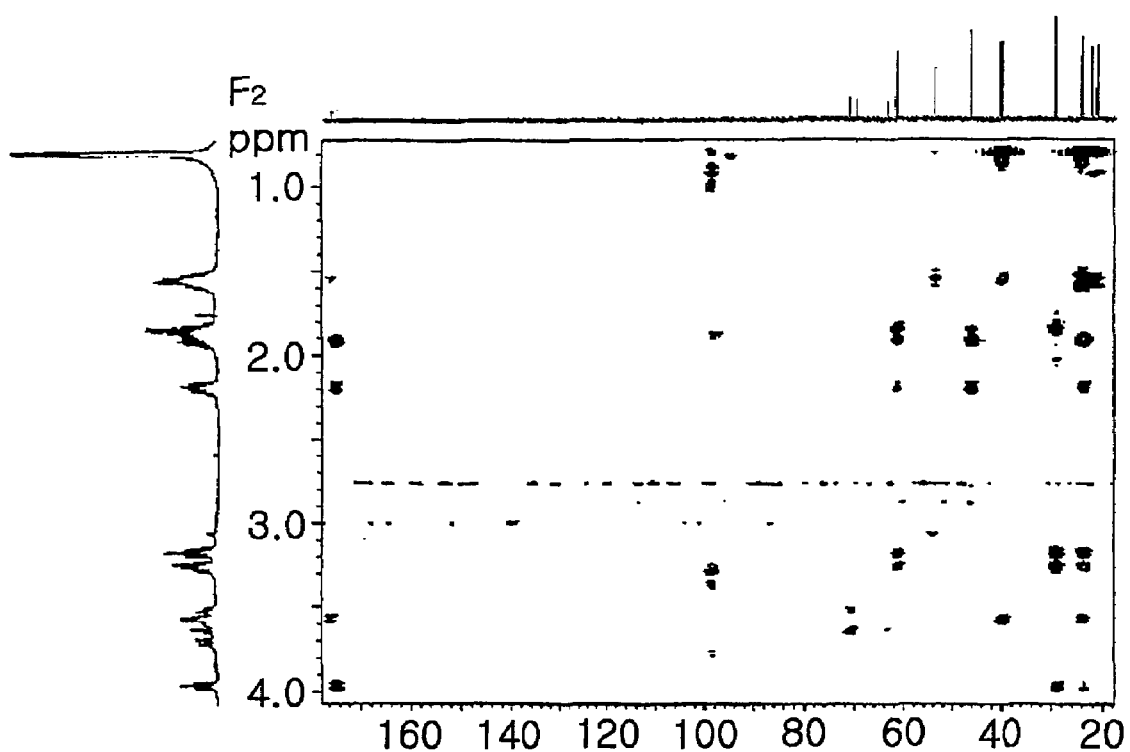
FIG. 24 is HMBC result to identify the chemical structure of the active material from the Dong 1-2-5 fraction of the aq. extract of the Tochu-kaso J300.

The samples of the present examples are aqueous extract of Tochu-kaso J300 after HPLC. The result obtained by using the 3-[5-(methoxy-ethyl)-3,6-dioxo-piperazine-2-yl]propionic acid is shown in FIG. 11 and the result obtained by using the 4-methyl-2-[(pyrolidine-2-carbonyl)-2-amino]pentanoic acid is shown in FIG. 18.

3. Comparison of Anti-HIV Active Component and Non-Active Component

When the extracts of Tochu-kaso J300 are performed the above analysis, the results are different according to the existence of the active component.

When the host cells, T-cells, are infected with HIV, most of the cells are destructed (died). However, when a sample contains anti-HIV active components, cell survivability increases as the concentration of the sample increases.

4. Functional Mechanism of the Active Component

Figure 7:
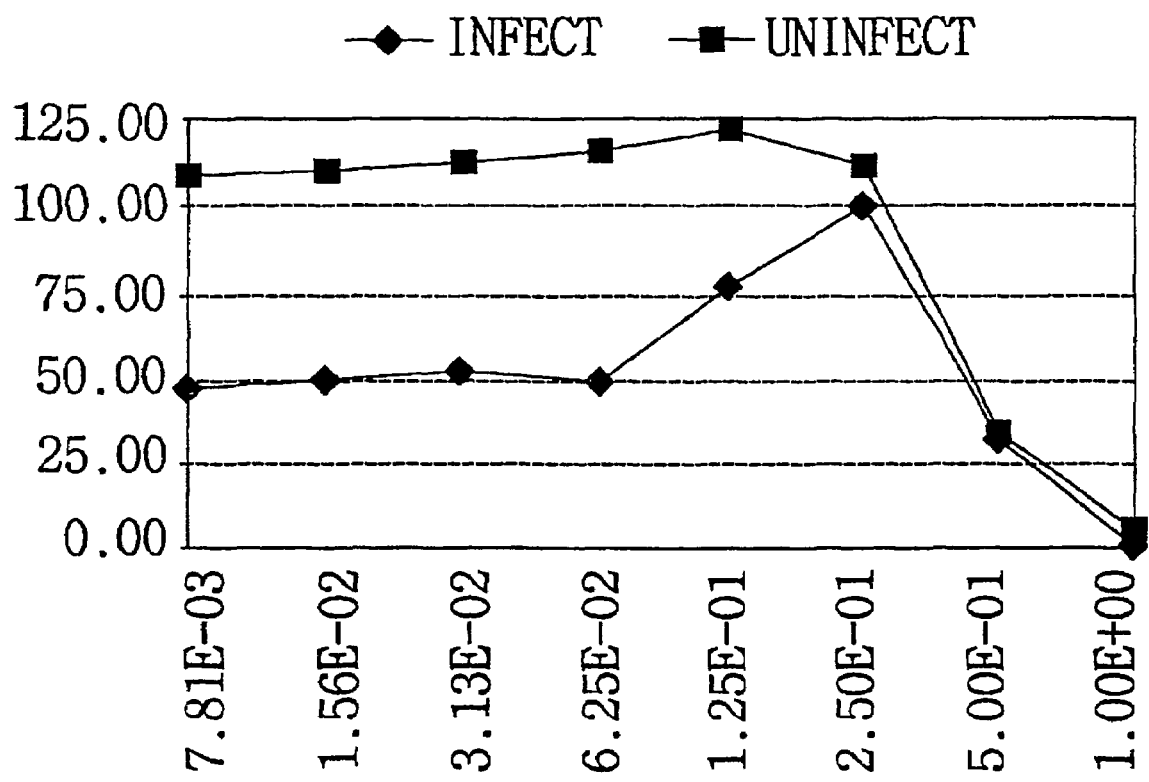
FIG. 7 shows the activation when virus is infected after incubating the aq. extract of the Tochu-kaso J300 and cells for 30 minutes.

To determine whether a material functions or not in the cell, the mixture of cell and sample is incubated for 30 minutes then infected with virus. The case that, Tochu-kaso J300 fraction of Dong 1-2-4 is added to the cell and infected with virus after 30 minute later, showed activity. Further, the case that, Tochu-kaso J300 fraction of Dong 1-2-5 is added to the cell and infected with virus after 30 minute later, also showed activity. In these case, the samples permeate the membranes of the cell and suppress the propagation of the virus in the cell, as well as the samples attach on the surface of the cell and suppress the introduction of the virus into the cell (FIG. 7)

Figure 8:
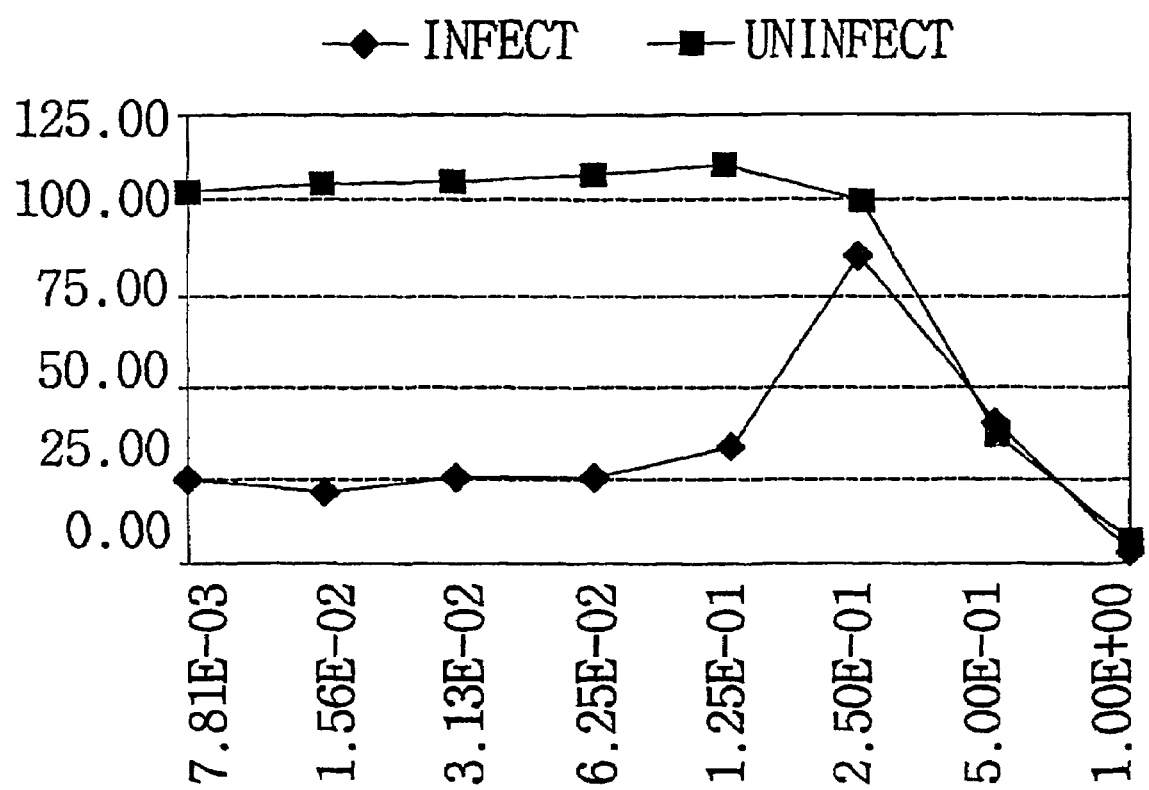
FIG. 8 shows the activation when the aq. extract of the Tochu-kaso J300 is added when 30 minutes has passed since the virus is infected.

In addition, after the cell was infected with the virus and incubated for 30 minutes, then the extracts of Tochu-kaso J300 were administered. If the functional site of the active material is out of the cell, the anti-HIV activity would not be detected; on the other hand, if the functional site is in the cell, the activity would be detected. In this experiment, the activation was detected. This proves that the active material suppresses the propagation of the virus in the cell, even when the sample is administered after a long time after the infection of the cell with virus (FIG. 8).

Example 4

Measurement of Toxicity With Transgenic Mouse

With transgenic mice that are treated to have HIV activity only in brain by genetic engineering, in vivo experiment was performed.

Fhe subacute test was performed by administrating the aqueous extracts of Tochu-kaso J300 containing the compounds of the present invention orally and via intravenous injection.

Figure 9:
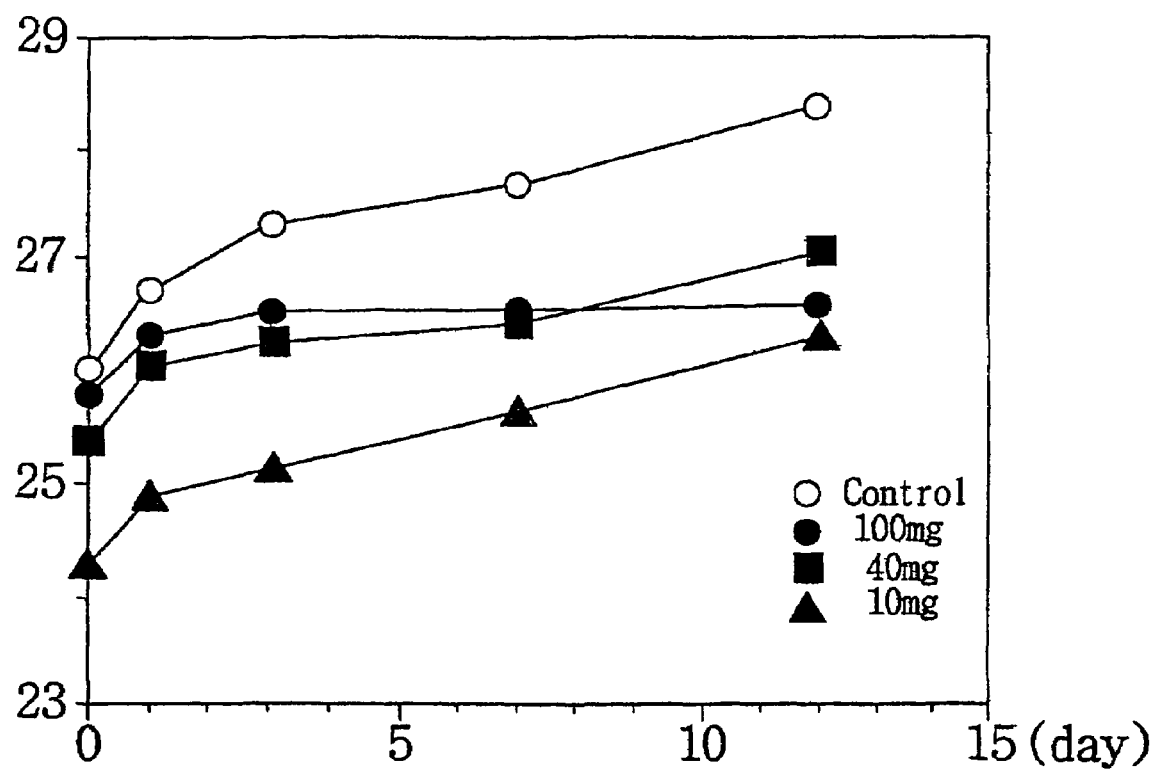
FIG. 9 shows the variations of the body weights of mice after oral dosage of the aq. extract of the Tochu-kaso J300.

In the oral administration, the tests were performed with the administration groups of 100 mg, 40 mg, 10 mg and no administration (normal). In a group of 100 mg administration, the increase of body weight was paralyzed, which implies the least toxicity to the mouse, and outer signs such as motility and diet were not changed. Observing the change of body weight, no side effect was detected to the 40 mg administration (FIG. 9). The results are shown in table 1.

TABLE 1

| Group | day | Body Weight (g) | | | | Ave ± SD |
|---|---|---|---|---|---|---|
| Normal | 0 | 25.0 | 28.0 | 24.0 | 27.0 | 26.0 ± 1.8 |
| Normal | +1 | 25.5 | 28.5 | 25.0 | 28.0 | 26.7 ± 1.8 |
|  | +3 | 28.5 | 26.0 | 29.5 | 28.5 | 27.3 ± 1.9 |
|  | +7 | 28.5 | 27.0 | 29.5 | 25.5 | 27.6 ± 1.8 |
|  | +12 | 30.0 | 28.0 | 25.5 | 29.5 | 28.3 ± 2.0 |
| 100 mg | 0 | 27.5 | 24.0 |  |  | 25.8 ± 2.5 |
|  | +1 | 28.5 | 24.0 |  |  | 26.3 ± 3.2 |
|  | +3 | 29.0 | 24.0 |  |  | 26.5 ± 3.5 |
|  | +7 | 29.0 | 24.5 |  |  | 26.5 ± 3.5 |
|  | +12 | 29.0 | 24.5 |  |  | 26.5 ± 3.5 |

TABLE 1-continued

| Group | day | Body Weight (g) | | | | | Ave ± SD |
|---|---|---|---|---|---|---|---|
| 40 mg | 0 | 23.5 | 26.0 | 26.5 | 24.0 | 27.0 | 25.4 ± 1.6 |
| | +1 | 27.5 | 23.5 | 24.5 | 26.5 | 28.0 | 26.0 ± 1.9 |
| | +3 | 24.0 | 26.5 | 25.0 | 27.0 | 28.5 | 26.2 ± 1.8 |
| | +7 | 27.5 | 28.5 | 25.0 | 24.0 | 27.0 | 26.4 ± 1.9 |
| | +12 | 25.0 | 25.5 | 27.5 | 29.5 | 27.0 | 27.0 ± 1.8 |
| 10 mg | 0 | 23.5 | 24.0 | 24.5 | 25.0 | | 24.3 ± 0.6 |
| | +1 | 24.5 | 24.5 | 25.0 | 25.5 | | 24.9 ± 0.5 |
| | +3 | 25.0 | 24.5 | 25.5 | 25.5 | | 25.1 ± 0.5 |
| | +7 | 25.0 | 25.0 | 26.5 | 26.0 | | 25.6 ± 0.8 |
| | +12 | 27.0 | 26.0 | 26.5 | 25.5 | | 26.3 ± 0.7 |

Figure 10:
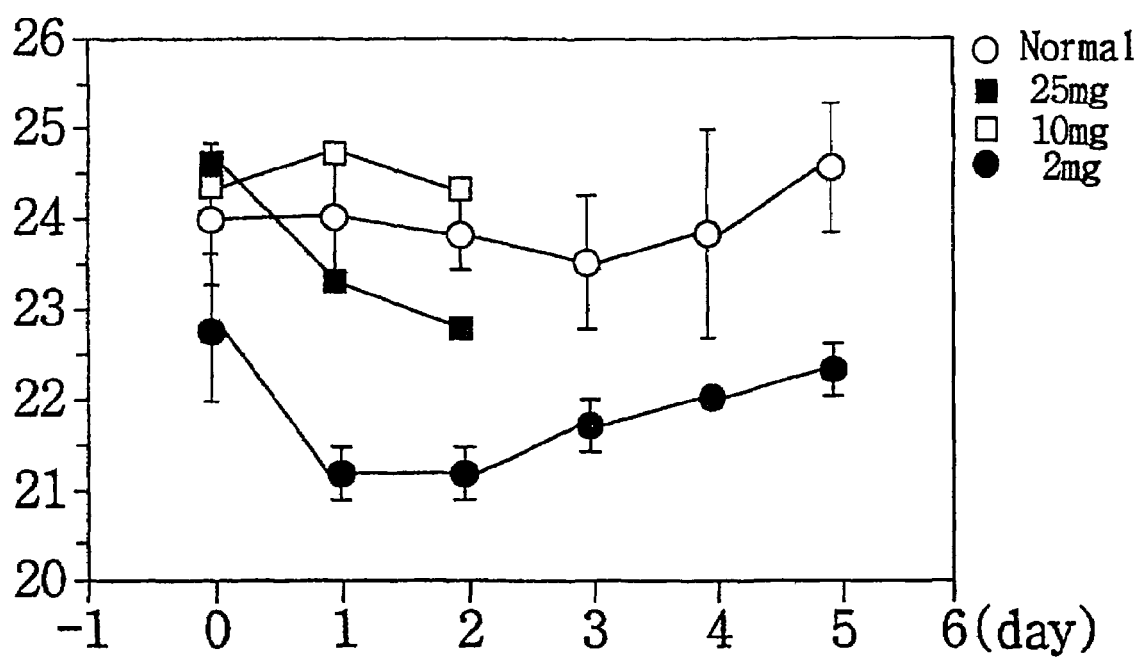
FIG. 10 shows the fatal dose of the aq. extract of the Tochu-kaso J300 to the HIV infected mouse and LD50 of a mouse administered with them.

In case of administration via intravenous injection, the tests were performed with the administration groups of 50 mg, 25 mg, 10 mg, 2 mg and no administration (normal). In a group of 50 mg administration, mouse was died just after the administration. In a group of 25 mg administration, after 1 week of administration, body weight was decreased, and some mice lost their sense of equilibrium and laid down on the ground and others also lost their mobility and died after 3 days of administration. In groups of 25 mg and 10 mg administration, the mice did not show such symptom as erection of their hairs. In a group of 2 mg administration, significant outer change was not detected, but the body weight was decreased for 1 week, however, the body weight increased later (FIG. 10). The results are shown in table 2.

TABLE 2

| Group | day | Body Weight (g) | | | Ave ± SD | note |
|---|---|---|---|---|---|---|
| Normal | 0 | 24.5 | 23.5 | | 24.0 ± 0.7 | |
| | +1 | 24.5 | 23.5 | | 24.0 ± 0.7 | |
| | +3 | 24.0 | 23.5 | | 28.3 ± 0.4 | |
| | +4 | 24.5 | 23.0 | | 23.8 ± 1.1 | |
| | +5 | 25.0 | 24.0 | | 24.5 ± 0.7 | |
| 50 mg | 0 | dead | dead | dead | | Died after 30 sec. of injection |
| 25 mg | 0 | 25.0 | 26.0 | 22.5 | 24.5 ± 1.8 | Some lose equilibrium sense |
| | +1 | 23.5 | 24.5 | 22.0 | 23.3 ± 1.3 | Losing mobility |
| | +2 | 24.0 | 21.5 | dead | 22.8 ± 1.8 | |
| | +3 | dead | dead | dead | | |
| 10 mg | 0 | 24.0 | 24.0 | 25.0 | 24.3 ± 0.6 | Normal state |
| | +1 | 24.5 | 25.5 | 24.0 | 24.7 ± 0.8 | Normal state |
| | +2 | 23.5 | 25.5 | 24.0 | 24.3 ± 1.0 | Losing mobility |
| | +3 | dead | dead | dead | | |
| 2 mg | 0 | 23.0 | 22.0 | 23.5 | 22.8 ± 0.8 | |
| | +1 | 21.0 | 21.0 | 21.5 | 21.2 ± 0.3 | |
| | +2 | 21.0 | 21.0 | 21.5 | 21.2 ± 0.3 | |
| | +3 | 22.0 | 21.5 | 21.5 | 21.7 ± 0.3 | |
| | +4 | 22.0 | 22.0 | 22.0 | 22.0 ± 0.0 | |
| | +5 | 22.5 | 22.0 | 22.5 | 22.3 ± 0.3 | |

Example 5

Preparation of 3-[5-(methoxy-ethyl)-3,6-dioxo-piperazine-2-yl]propionic acid (Organic Synthesis)

1) Amination of L-Boc-Glu and L-Threonine

Preparation of 2-(2-tert-butoxycarbonylamino-4-methoxycarbonyl-butyrylamino)-3-hydroxy-butyric acid methyl ester 240 mg (0.919 mmol) of L-Boc-glutamic acid 5-methyl-ester and 195 mg (1.19 mmol) of 3-hydroxy-benzo-triazine-2(H)-4-one were dissolved in 3 mL of anhydrous methylenechloride (MC). DCC 247 mg (1.19 mmol) was added under $N_2$ and ice cooled and stirred for 10 minutes. A solution of L-threonine methyl ester hydrochloride 171 mg (1.01 mmol) and TEA 169 μL in 2 mL anhydrous MC was added to the above solution and stirred for 3 hours. The mixture was filtered off urea and the filtrate extracted with MC and water. The organic layer extracted twice with sat. $NaHCO_3$ and brine. The organic extract was dried ($Mg_2SO_4$) and then evaporated. The final product was purified on silica gel column using hexane:ethylacetate=2:1.

Analysis was performed. Column chromatography was performed on Merck Silica Gel 60 (70-230 mesh). TLC was carried out using glass sheets precoated with silica gel 60 $F_{254}$ prepared by E. Merck. All the commercially available reagent chemicals were obtained from Aldrich, Fluka and Tokyo Kasei Chemical Company and generally used without further purification. Solvents were distilled over appropriate drying materials before use. Same analysis was performed hereinafter.

The analysis results of the product, GT-2 ([2-(2-tert-butoxycarbonylamino-4-methoxycarbonyl-butylamino)-3-hydroxy-butyric acid methyl ester]), are as follows.

Yield 340 mg (94%)

Rf 0.55 (EA)

$^1$H NMR ($CDCl_3$, 300 MHz) δ 7.31 (d, 1H, J=8.4 Hz), 5.54 (d, 1H, J=7.8 Hz), 4.54 (dd, 1H, J=2.5, 9.0 Hz), 4.29 (m, 2H), 3.72 (s, 3H), 3.70 (s, 3H), 2.43 (t, 2H, J=7.3 Hz), 2.09 (m, 1H), 1.93 (m, 1H), 1.38 (s, 9H), 1.16 (d, 3H, J=5.0 Hz)

2) Removal of BOC Group (GT-3)

Preparation of 2-(2-Amino-4-methoxycarbonyl-butyrylamino)-3-hydroxy-butyric acid methyl ester A solution of GT-2 100 mg (0.266 mmol) in 5 mL $CH_2Cl_2$ was treated with TFA 72 μL (0.932 mmol) and stirred at room temperature for 12 hours. Then, the solvent was evaporated to dryness.

The analysis results of the product, GT-3 [2-(2-Amino-4-methoxycarbonyl-butyrylamino)-3-hydroxy-butyric acid methyl ester], are as follows.

Rf 0.40 (EA:MeOH=3:1)

$^1$H NMR ($D_2O$, 300 MHz) δ 5.00 (m, 1H), 4.84 (m, 1H), 4.64 (m, 1H), 4.21 (s, 3H), 4.19 (s, 3H), 3.05 (t, 2H, J=7.4 Hz), 2.66 (m, 2H), 1.63 (d, 3H, J=6.6 Hz)

3) Cyclization (GT-4)

Preparation of 3-[5-(1-hydroxy-ethyl)-3,6-dioxopiperazin-2-yl]-propionic acid methyl ester A solution of GT-3 50 mg (0.181 mmol) in 3 mL THF was treated with TEA 151 μL (1.09 mmol) and stirred at room temperature for 12 hours. The mixture extracted with MC and water. The aqueous layer extracted twice with MC. The organic extract was dried with $Mg_2SO_4$ and then evaporated. The final product was purified on silica gel column using hexane:ethylacetate=4:1.

The analysis results of the product, GT-4 (3-[5-(1-hydroxy-ethyl)-3,6-dioxo-piperazin-2-yl]-propionic acid methyl ester), are as follows.

Rf 0.67 (EA)

$^1$H NMR ($CDCl_3$, 300 MHz) δ 7.67 (d, 1H, J=4.1 Hz), 7.30 (d, 1H, J=8.9 Hz), 4.64 (dd, 1H, J=7.8, 12.8 Hz), 4.53 (d, 1H, J=8.9 Hz), 4.40 (m, 1H), 3.80 (s, 3H), 3.68 (s, 3H), 2.51 (m, 2H), 2.21 (m, 1H), 2.04 (m, 1H), 1.20 (d, 3H, J=6.5 Hz)

4) Decarboxylation (GT-5) and Methylation

Preparation of 3-[5-(1-Hydroxy-ethyl)-3,6-dioxo-piperazin-2-yl]-propionic acid and 3-[5-(methoxy-ethyl)-3,6-dioxo-piperazine-2-yl]propionic acid A solution of GT-4 35 mg (0.146 mmol) in $H_2O$ was treated with 20% NaOH 1 mL and stirred at room temperature for 30 min. Then, the solvent was evaporated to dryness. The final product was purified to obtain GT-5. Then, the GT-5 was methylated to obtain 3-[5-(methoxy-ethyl)-3,6-dioxo-piperazine-2-yl]propionic acid.

In the above purification, silica gel column using ethyl acetate MeOH=2:1 was used. Further, the analysis results of the product, GT-5 (3-[5-(1-Hydroxy-ethyl)-3,6-dioxo-piperazin-2-yl]-propionic acid), are as follows.

Rf 0.12 (ethyl acetate/methanol=1:3)

$^1$H NMR ($D_2O$, 300 MHz) δ 4.19 (m, 2H), 3.90 (t, 1H, J=6.5 Hz), 2.36 (m, 2H), 2.05 (m, 2H), 1.20 (d, 3H, J=6.2 Hz)

Example 6

Preparation of 4-methyl-2-[(pyrolidine-2-carbonyl)-2-amino]pentanoic acid (Organic Synthesis)

1) Amination of L-Boc-Proline and L-Leucine (LP-3)

Preparation of 2-(1-Methoxycarbonyl-3-methyl-butylcarbamoyl)-pyrrolidine-1-carboxylic acid tert-butyl ester L-Boc-Proline 50 mg (0.232 mmol) and 3-hydroxy-benzotriazine-2(H)-4-one 45 mg (1.2 mmol) were dissolved in 3 mL anhydrous MC. DCC 57 mg (1.2 mmol) was added under $N_2$ and ice cooled and stirred for 10 minutes. A solution of L-leucine methyl ester 51 mg (0.278 mmol) and TEA 38 μL (0.278 mmol) in a little anhydrous DMF and 3 mL anhydrous MC was added to the above solution and stirred for 15 hours. The mixture was filtered off urea and the filtrate extracted with MC and water. The aqueous layer extracted twice with MC. The organic extract was dried ($Mg_2SO_4$) and then evaporated. The final product was purified on silica gel column using hexane:ethylacetate=4:1. The analysis results of the product, LP-3 [2-(1-Methoxycarbonyl-3-methyl-butylcarbamoyl)-pyrrolidine-1-carboxylic acid tert-butyl ester], are as follows.

Rf 0.67 (EA)

$^1$H NMR ($CDCl_3$, 300 MHz) δ 7.36 (m, 1H), 4.52 (m, 1H), 4.27 (m, 1H), 3.72 (s, 3H), 3.31 (m, 2H), 2.17-1.59 (m, 7H), 1.46 (s, 9H), 0.91 (d, 6H, J=5.8 Hz)

2) Removal of BOC Group (LP-4)

Preparation of 4-Methyl-2-[(pyrrolidine-2-carbonyl)-amino]-pentanoic acid methyl ester A solution of LP-3 50 mg (0.146 mmol) in $CH_2Cl_2$ was treated with TFA 39 μL (0.511 mmol) and stirred at room temperature for 12 hours. Then, the solvent was evaporated to dryness. The final product was purified on silica gel column using ethylacetate: MeOH=20:1. The analysis results of the product, LP-4 [4-Methyl-2-[(pyrrolidine-2-carbonyl)-amino]-pentanoic acid methyl ester], are as follows.

Rf 0.27 (EA:MeOH=3:1)

$^1$H NMR ($CDCl_3$, 300 MHz) δ 8.30 (d, 1H, J=7.5 Hz), 4.69 (t, 1H, J=7.3 Hz), 4.45 (dd, 1H, J=3.0, 7.3 Hz), 3.70 (s, 3H), 3.39 (m, 2H), 2.43 (m, 1H), 2.10 (m, 2H), 2.01 (m, 1H), 1.62 (m, 3H), 0.90 (d, 3H, J=5.9 Hz), 0.88 (d, 3H, J=5.7 Hz)

3) Hydrolysis (LP-5)

Preparation of 4-Methyl-2-[(pyrrolidine-2-carbonyl)-2-amino]pentanoic acid

A solution of LP-4 35 mg (0.146 mmol) in $H_2O$ was treated with 20% NaOH (1 mL) and stirred at room temperature for 30 min. Then, the solvent was evaporated to dryness. The final product was purified on silica gel column using ethylacetate MeOH=2:1. The analysis results are as follows.

Rf 0.24 (ethyl acetate/methanol=1:3)

$^1$H NMR ($D_2O$, 300 MHz) δ 4.20 (m, 2H), 3.76 (m, 1H), 3.24 (m, 1H), 2.36-1.58 (m, 7H), 0.88 (d, 3H J=5.7 Hz), 0.87 (d, 3H, J=6.5 Hz)

As described above, the extract of Tochu-kaso J300 of the present invention shows ant-HIV activity. Especially, 3-[5-(methoxy-ethyl)-3,6-dioxo-piperazine-2-yl]propionic acid and 4-methyl-2-[(pyrrolidine-2-carbonyl)-2-amino]pentanoic acid that can be extracted from Tochu-kaso J300 have low toxicity and low side effects compared with conventional AIDS treatment, and therefore, can be used as drug and food additives.

The invention claimed is:

1. A method of inhibiting HIV activity comprising administering to a subject in need of same an HIV-inhibiting amount of 3-[5-(methoxy-ethyl)-3,6-dioxo-piperazine-2-yl]propionic acid, as represented by the following Formula 1, and 4-methyl-2-[(pyrrolidine-2-carbonyl)-2-amino]pentanoic acid, as represented by the following Formula 2

[Formula 1]

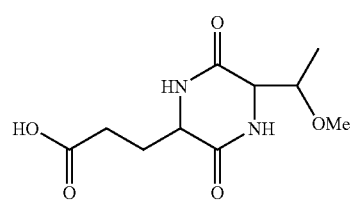

[Formula 2]

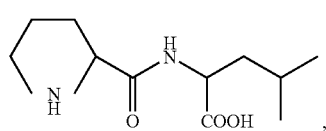

wherein 3-[5-(methoxy-ethyl)-3,6-dioxo-piperazine-2-yl] propionic acid and 4-methyl-2-[(pyrrolidine-2-carbonyl)-2-amino]pentanoic acid are purified, or are obtained by organic synthesis.

2. A method of inhibiting HIV activity comprising administering to a subject in need of same an HIV-inhibiting amount of 3-[5-(methoxy-ethyl)-3,6-dioxo-piperazine-2-yl]propionic acid, as represented by the following Formula 1

[Formula 1]

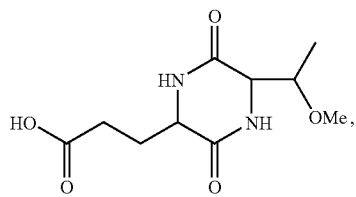

wherein 3-[5-(methoxy-ethyl)-3,6-dioxo-piperazine-2-yl] propionic acid is purified, or is obtained by organic synthesis.

3. A method of inhibiting HIV activity comprising administering to a subject in need of same an HIV-inhibiting amount of 4-methyl-2-[(pyrrolidine-2-carbonyl)-2-amino]pentanoic acid, as represented by the following Formula 2

[Formula 2]

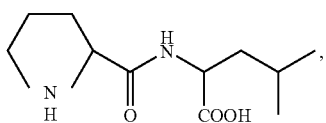

wherein 4-methyl-2-[(pyrrolidine-2-carbonyl)-2-amino] pentanoic acid is purified, or is obtained by organic synthesis.

* * * * *